United States Patent
Fakhrai-Rad et al.

(10) Patent No.: US 9,910,962 B1
(45) Date of Patent: Mar. 6, 2018

(54) GENETIC AND ENVIRONMENTAL RISK ENGINE AND METHODS THEREOF

(71) Applicants: Hossein Fakhrai-Rad, Los Altos, CA (US); Keyan Salari, Boston, MA (US); Dara Patrick Dowlatshahi, Palo Alto, CA (US); Abdolkarim Pourak, Suwanee, GA (US); Harshna Harshvadan Kapashi, Mountain View, CA (US); Malekeh Amini, Menlo Park, CA (US); Pouria Mojabi, San Francisco, CA (US); Celine Becquet, Mountain View, CA (US); Prakash Menon, Cupertino, CA (US); Mehrdad Rezaee, Los Altos, CA (US)

(72) Inventors: Hossein Fakhrai-Rad, Los Altos, CA (US); Keyan Salari, Boston, MA (US); Dara Patrick Dowlatshahi, Palo Alto, CA (US); Abdolkarim Pourak, Suwanee, GA (US); Harshna Harshvadan Kapashi, Mountain View, CA (US); Malekeh Amini, Menlo Park, CA (US); Pouria Mojabi, San Francisco, CA (US); Celine Becquet, Mountain View, CA (US); Prakash Menon, Cupertino, CA (US); Mehrdad Rezaee, Los Altos, CA (US)

(73) Assignee: BASEHEALTH, INC., Redwood, CA (US)

( * ) Notice: Subject to any disclaimer, the term of this patent is extended or adjusted under 35 U.S.C. 154(b) by 1014 days.

(21) Appl. No.: 14/104,861

(22) Filed: Dec. 12, 2013

Related U.S. Application Data

(60) Provisional application No. 61/755,462, filed on Jan. 22, 2013, provisional application No. 61/755,463,
(Continued)

(51) Int. Cl.
*G06F 7/60* (2006.01)
*G06F 17/10* (2006.01)
(Continued)

(52) U.S. Cl.
CPC .......... *G06F 19/3431* (2013.01); *G06F 17/50* (2013.01)

(58) Field of Classification Search
None
See application file for complete search history.

(56) References Cited

U.S. PATENT DOCUMENTS

2006/0099610 A1* 5/2006 Salonen ............... C12Q 1/6883
435/6.11
2009/0249498 A1* 10/2009 Stephan ............. A61K 31/7088
800/3
(Continued)

*Primary Examiner* — Cedric D Johnson
(74) *Attorney, Agent, or Firm* — Squire Patton Boggs

(57) ABSTRACT

Risk engines and related methods may benefit patients and their physicians. For example, patients may benefit from being able to determine their personal genetic, environmental, and behavioral risks. Moreover, physicians may be able to provide statistically-driven individual recommendations based on a risk engine's determination of such risks. A method can include selecting one or more candidate genetic variants associated with a phenotype from the scientific literature. The method can also include scoring a genetic association between the one or more candidate genetic variants and the phenotype. The method can further include selecting one or more high-scoring genetic variants. Selecting a best genetic variant within each of at least one linkage disequilibrium (LD) block can also be included in the method. The method can additionally include calculating risk associated with the best genetic variant from the at least one LD block.

6 Claims, 22 Drawing Sheets

Related U.S. Application Data filed on Jan. 22, 2013, provisional application No. 61/755,465, filed on Jan. 22, 2013, provisional application No. 61/755,466, filed on Jan. 22, 2013.

(51) Int. Cl.
  *G06F 19/00* (2018.01)
  *G06F 17/50* (2006.01)

(56) References Cited

U.S. PATENT DOCUMENTS

| | | | |
|---|---|---|---|
| 2010/0070455 A1* | 3/2010 | Halperin | G06F 19/18 706/54 |
| 2011/0010148 A1* | 1/2011 | Ragot | A01H 1/04 703/2 |

* cited by examiner

| SNP | Genotype | Disease | OddsRatio | Population Frequency |
|---|---|---|---|---|
| rs1234 | AA | Stroke | 1(reference) | F1 |
| rs1234 | AG | Stroke | D | F2 |
| rs1234 | GG | Stroke | E | F3 |

Figure 2

| haplotype allele | Odd ratio | Freq Case | Freq Control |
|---|---|---|---|
| A | $\dfrac{p_a(1-p_u)}{(1-p_a)p_u}$ | $p_a$ | $p_u$ |
| B | $\dfrac{q_a(1-q_u)}{(1-q_a)q_u}$ | $q_a$ | $q_u$ |
| C | $\dfrac{r_a(1-r_u)}{(1-r_a)r_u}$ | $r_a$ | $r_u$ |

Figure 3

| Blood Pressure | Odds Ratio | Confidence Interval (CI) |
|---|---|---|
| 115-120 | 1 | reference |
| 120-130 | 1.5 | [1.1-2] |
| 130-140 | 2 | [1.5-3] |

Figure 6

```
glm(formula = CVD ~ BMIC2 + Age + Gender + WaistAdBMI2 + Race,
    family = binomial, data = Data1)

Deviance Residuals:
    Min       1Q   Median       3Q      Max
-0.7320  -0.2955  -0.1613  -0.0837   3.8650

Coefficients:
              Estimate Std. Error z value Pr(>|z|)
(Intercept) -9.252646   0.777788 -11.896  < 2e-16 ***
BMIC2        0.064821   0.011524   5.625 1.85e-08 ***
Age3         1.883263   0.759363   2.480  0.01314 *
Age4         2.720815   0.726350   3.746  0.00018 ***
Age5         3.495981   0.719462   4.859 1.18e-06 ***
Age6         4.099682   0.713808   5.743 9.28e-09 ***
Age7         4.473912   0.713955   6.266 3.70e-10 ***
Age8         5.147710   0.712539   7.224 5.03e-13 ***
GenderM     -0.075031   0.103354  -0.726  0.46786
WaistAdBMI2  0.019773   0.007346   2.692  0.00711 **
Race2Hisp    0.010918   0.118142   0.092  0.92637
Race3NHBlack 0.441559   0.113831   3.913 9.10e-05 ***
Race4Other   0.330240   0.252858   1.306  0.19154
---
Signif. codes:  0 '***' 0.001 '**' 0.01 '*' 0.05 '.'

(Dispersion parameter for binomial family taken to be 1)

Null deviance: 5077.3  on 18866  degrees of freedom
Residual deviance: 4381.9  on 18854  degrees of freedom
AIC: 4407.9

Number of Fisher Scoring iterations: 9
```

Figure 8

GENETIC AND ENVIRONMENTAL RISK ENGINE AND METHODS THEREOF

BACKGROUND

Field

Risk engines and related methods may benefit patients and their physicians. For example, patients may benefit from being able to determine their personal genetic, environmental, and behavioral risks. Moreover, physicians may be able to provide statistically-driven individual recommendations based on a risk engine's determination of such risks. By determining the components of an individual's disease risk and making evidence-based recommendations, patients can be empowered to make behavioral changes that can reduce their disease risks to the greatest extent possible.

Description of the Related Art

The sources of common diseases and conditions are typically attributed to genetic, environmental, and behavioral factors. With the goal of understanding existing and new associations between diseases and genetic variants across the genome, many genome-wide association studies have been completed in recent years. However, applications of these genetic associations with disease are few.

Assessing the risks of diseases can be useful in disease prevention. The risk of a disease can be the probability that an individual will develop the disease in a given period of time. The risk of a disease may depend on multiple risk factors including both genetic factors and non-genetic factors. The risk of a disease may be predicted using statistical risk prediction models determined from statistical analysis of sample data comprising measurements of the relevant risk factors from a given population.

Non-genetic factors can refer to factors that are not measured by genotyping. These factors can include age, sex, race, family history, height and weight, as well as environmental factors. These can also be values of measurable parameters such as blood pressure, heart rate, blood test results, and the like, or parameters that are deduced from other measurable parameters such as body mass index (BMI), which is the weight of the patient divided by the squared value of the patient's height ($kg/m^2$).

To assess the state of a patient's health and counsel a patient on how to adopt a healthier lifestyle, a healthcare practitioner must integrate all relevant health data on the patient, including the patient's behaviors, environmental exposures and laboratory test results, to devise an effective plan tailored to the patient. This process is often practitioner-dependent. For example, one practitioner may be a dietician that advises dieting and exercise methods under a framework that assumes the BMI of a female under the age of sixty should not exceed the value of 25, whereas a second dietitian may only consider intervening when the patient reaches a level of obesity defined as a BMI of 30 or greater. Each practitioner may also recommend very different dieting and exercise programs or methods. This means that the same patient with the same health data at the same point in time may receive different recommendations for the same risk factor depending on which practitioner provides the assessment and plan. This is partially due to the fact that integrating vast amounts of data in a consistent, systematic way across many different patients can be difficult to do and is prone to inter- and intra-practitioner variation.

SUMMARY

Certain embodiments of the present invention may employ a method, the method comprising selecting one or more candidate genetic variants associated with a phenotype; scoring a genetic association between the one or more candidate genetic variants and the phenotype; selecting one or more high-scoring genetic variants; selecting a best genetic variant within each of at least one linkage disequilibrium (LD) block; and calculating risk associated with the best genetic variant from the at least one LD block.

Additional embodiments of the present invention may provide an apparatus, the apparatus comprising at least one processor; and at least one memory including computer program code, wherein the at least one memory and the computer program code are configured to, with the at least one processor, cause the apparatus at least to select one or more candidate genetic variants associated with a phenotype; score a genetic association between the one or more candidate genetic variants and the phenotype; select one or more high-scoring genetic variants; select a best genetic variant within each of at least one LD block; and calculate risk associated with the best genetic variant from the at least one LD block.

Further embodiments of the present invention may provide a non-transitory computer-readable medium encoded with instructions that, when executed in hardware, perform a process, the process comprising selecting one or more candidate genetic variants associated with a phenotype; scoring a genetic association between the one or more candidate genetic variants and the phenotype; selecting one or more high-scoring genetic variants; selecting a best genetic variant within each of at least one LD block; and calculating risk associated with the best genetic variant from the at least one LD block.

BRIEF DESCRIPTION OF THE DRAWINGS

For proper understanding of the invention, reference should be made to the accompanying drawings, wherein:

FIG. 2 is an exemplary data structure according to certain embodiments.

FIG. 3 is another exemplary data structure according to certain embodiments.

FIG. 6 is a schematic illustration showing a sample table extracted from an article, in accordance with certain embodiments.

FIG. 8 is a schematic illustration showing a sample result of statistical analysis in R language, in accordance with certain embodiments.

DETAILED DESCRIPTION

Certain embodiments may relate generally to assessing risks for multifactorial diseases, based on genetic, environmental and behavioral risk factors. Certain embodiments may, for example, provide early medical diagnostic information. For example, certain embodiments provide diagnostic computerized medical devices that can detect early genetic tendencies of developing certain diseases. More particularly, certain embodiments provide a computer-implemented method to compute genetic risks of developing a phenotype or disease given certain alleles of single nucleotide polymorphisms (SNPs), other forms of genetic variation, and/or haplotypes in a specific ethnicity or genetic background.

Certain embodiments may also provide a method and a system for tracking and evaluating how well a member or a set of members belonging to a care group is making efforts to achieve a healthier lifestyle.

Moreover, certain embodiments may provide methods and systems to capture the environmental and behavioral characteristics associated with a phenotype. Similarly, certain embodiments may provide methods and systems to identify the environmental risk factors for a phenotype.

Certain embodiments may provide methods and systems to calculate the associated risk of both simple and derived risk factors for a phenotype. Additionally, certain embodiments may provide methods and systems to calculate a special confidence of the risk assessment for a phenotype.

Sources of data for certain embodiments can include coverage of all the recently published scientific articles relevant to the environmental/behavioral and genetic risk factors associated to a phenotype. Moreover, certain embodiments can utilize public and frequently updated databases such as the National Health and Nutrition Examination Survey (NHANES) and other Centers for Disease Control and Prevention (CDC) resources.

Statistical analysis can be used to understand the correlation and, in certain instances, causality of identified factors to a phenotype of interest. Statistical analysis can also be used to develop risk assessment models composed of independent risk factors. Subgroup analysis by ethnicity can be used to model the genetic, environmental and behavioral risks separately for different ethnicities.

Multiple computer-implemented processes can be implemented. These processes can be integrated together or modularized, such that various combinations of the modules can be implemented in different embodiments.

Figure 1:
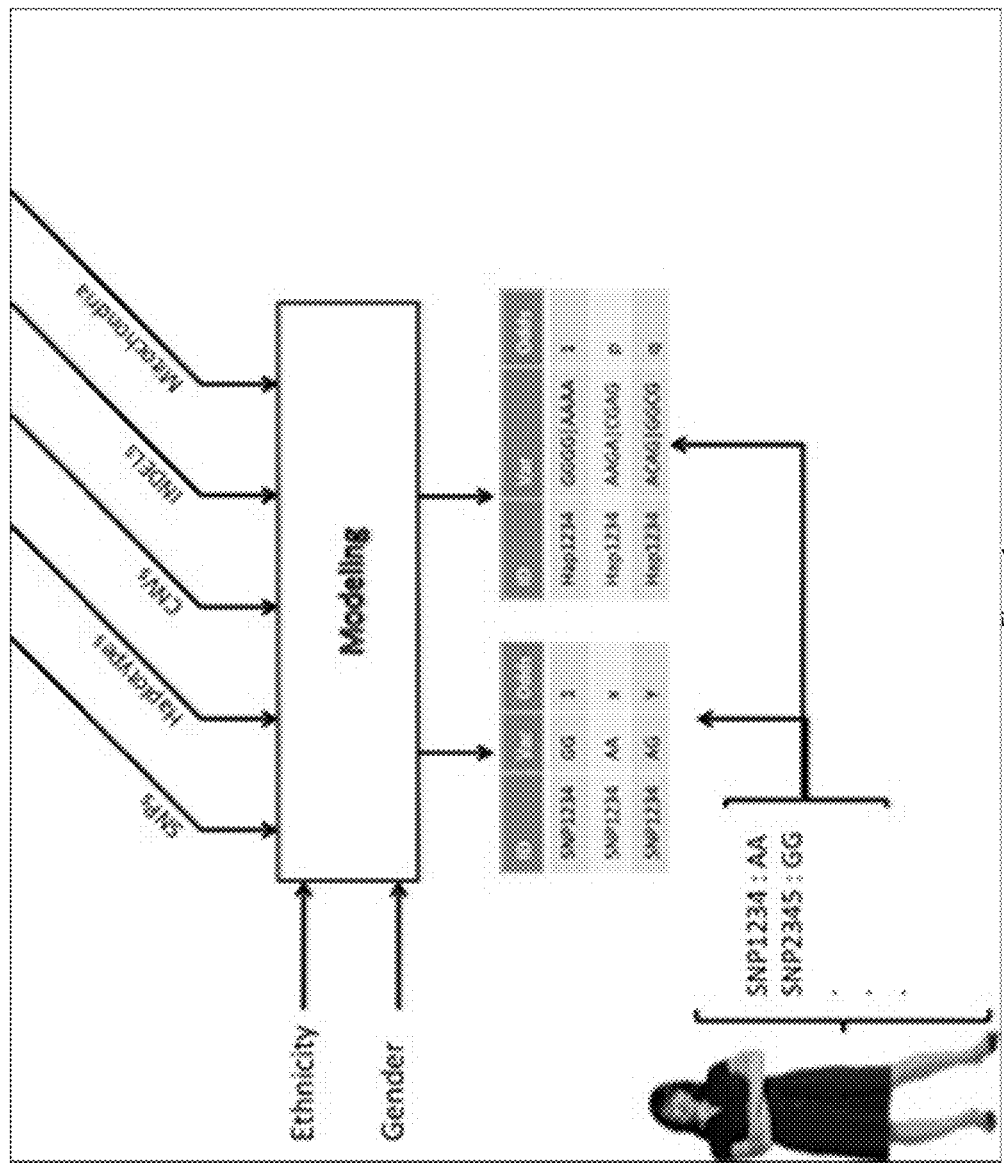
FIG. 1 is a diagram of a genetic risk engine according to certain embodiments.

FIG. 1 is a diagram of a genetic risk engine, where ethnicity, gender, and associated genome information in the form of SNPs, haplotypes, copy number variations (CNVs), insertions or deletions (indels), or mitochondrial DNA variants can serve as input data into the genetic risk engine, which sorts and selects the input data and generates a model for the genetic risk of developing a phenotype or disease. The model can be applied to an individual's genome information to determine his or her genetic risk.

To generate a model for the genetic risk of a given disease, the appropriate genetic variants must be selected as risk factors. In one embodiment, a variant selection process may be implemented. The input to the variant selection process can be the genetic association data obtained from published studies or public databases. The data recorded can be specific to a phenotype, a study, an ethnicity (for example, Caucasian, Asian, African, or the like), a variant, or a genetic model (for example, allelic, genotypic, haplotype, and/or additive, dominant, recessive).

Based on the input data, the variant selection process can select the most appropriate list of genetic variants and the specific association data that will be used to calculate the genetic risk of an individual from a given ethnicity for a given phenotype. This selection can be configured to ensure both independence and completeness.

The system can include a module that scores the evidence supporting a specific genetic variant's association to a given phenotype in a given ethnicity. The scoring module can evaluate the evidence based on replication (i.e., whether the association has been observed more than once), study type, study sample size, genetic models employed in the study and the strength of the association (i.e., P value). Based on these parameters, each genetic variant receives a score. When multiple genetic variants in the same LD block score highly, it can be that only the highest-scoring variant in a given LD block for which genotype data is available is used as part of an individual's genetic risk calculation (described below).

The genetic variant scoring module's functionality can be specific to a given phenotype and ethnicity, and can provide a method for selecting validated, scientifically robust genetic variants associated a given disease among those reported in the published scientific literature. In the first pass, the procedure can remove all variants whose association does not achieve genome-wide statistical significance (i.e., $P<5.0\times10^{-8}$ for genome-wide association studies; lower thresholds may be used for single gene association studies). Next, all variants that have been found to be associated with the given disease in the given ethnicity only once and not yet replicated (i.e., only found in a "discovery" study), can be removed. The remaining variants, all of which achieved genome-wide significance and have been replicated at least once in the given ethnicity, can be assigned a score based on the following criteria, in order of importance: (1) the study type(s) in which the variant association has been found (e.g., a meta-analysis scores higher than a replication/validation study); (2) the sample size of the study; (3) the genetic model employed in the study (i.e., genotype-based vs. allele-based); and (4) the strength of the association (i.e. P-value or confidence interval). This procedure assumes the entire relevant body of variant associations from the scientific literature is provided as input.

The genetic variant scoring module can be performed on the collection of all genetic variants (SNPs, CNVs, or other forms of genetic variation) under consideration that are putatively associated with a given disease in a given ethnicity. The procedure can be repeated for each ethnicity and each disease.

The module can also check that the allele and/or genotype frequencies are available from the study's control group and/or in the Haplotype Map (HapMap) sample representing the given ethnicity. This information can be used for computing population-adjusted odds ratios in downstream analysis.

Using the score outputs from the genetic variant scoring module, the high-scoring variants can be nominated for a given phenotype in a given ethnicity and considered to be of high quality and robustness. However, two or more high-scoring genetic variants may be nearby one another (i.e., in linkage disequilibrium). A linkage disequilibrium (LD) block can be considered to be a group of variants highly correlated with each other; thus, one representative variant captures nearly all the information for the variants in a given LD block. The system can select one representative variant from the LD block to be used in downstream calculations of the individual's genetic risk for the given disease in the given ethnicity. A standard for whether a genetic variant is high-scoring can be set by a user using a predetermined numeric threshold. Alternatively, the genetic variants with a score in a certain percentile, such as the $90^{th}$ percentile, among all candidate genetic variants can be considered high-scoring. The best high-scoring genetic variant in an LD block may be the highest scoring genetic variant in the LD block, or the genetic variant with the best correlation to other genetic variations in the LD block, or specifically a high scoring genetic variant with the best correlation to other high scoring genetic variations.

The LD blocks can be defined independently for each ethnicity using HapMap LD data, which is publicly available from the International HapMap Project. For each HapMap population/ethnicity, LD coefficients can be computed between pairs of nearby genetic variants. Pairs of variants with LD scores above a given threshold (e.g., $r^2>0.8$) can be considered to be in LD with one another.

When two or more high-scoring variants associated with the same disease in the same ethnicity are in LD with one another, one representative variant can be selected for downstream genetic risk calculations. Given each genetic variant is assigned a score in the genetic variant scoring module (described above), a representative variant can be selected based on the score, subject to availability of the variant genotype in the individual's genome data.

For example, an individual who undergoes genome sequencing may have genotype data for all of the genetic variants in a given LD block. In such cases, the highest-scoring variant can be selected for downstream analysis.

In another example, an individual who undergoes microarray-based genotyping may only have genotype data for a subset of the genetic variants in a given LD block. In such cases, the highest-scoring variant for which the individual has genotype data can be selected for downstream analysis.

The result of the selection process described above can be a set of genetic variants, with no more than one variant from a given LD block, associated with a given phenotype in a given ethnicity that have all achieved high quality scores based on the available scientific evidence. This set of genetic variants can then be used to calculate an individual's genetic risk for the given phenotype by the process described below.

A single nucleotide polymorphism (SNP) is one form of genetic variation that can be used for genetic risk calculation. SNP association data can be extracted from publications where a given phenotype was studied in a specific ethnicity using a specific genetic model. GWAS can be a source for this type of genetic association data. A computer data structure, like the one in FIG. 2, can be created to store this information for the risk engine's access.

FIG. 2 is an exemplary data structure that may be used by the genetic risk engine to compute the risk or odds ratio conferred by the alleles of a given genetic variant. The sample data structure illustrates that for the association between SNP rs1234 and stroke, the "AA" serves as the reference genotype and the OR for individuals with genotypes "AG" and "GG" will be computed relative to the reference genotype. That is, the result of the computation will provide the odds of developing the phenotype for each possible genotype compared to the reference genotype. The data structure also contains the population frequency for each genotype to indicate the prevalence of the genotype in the given population.

To calculate the odds ratio (OR) for each genotype, one genotype can be selected as the reference genotype, which is defined as an OR of 1.0. The OR for the other genotypes can be computed using the following formula:

$$OddsRatio = \frac{\frac{p}{1-p}}{\frac{p_{ref}}{1-p_{ref}}}$$

where p=P(D|G) is the probability of developing a disease given genotype G, and the odds of developing the disease given the genotype G is p/(1−p). This odds ratio can quantify the likelihood of developing a disease for each genotype compared to the reference genotype.

Also included in the data structure can be the population frequency of each genotype. The product of each genotype frequency and the respective genotype-specific disease probability [P(D|G)] can sum up to the overall average probability of developing the disease in the given population, which is equivalent to the population-specific disease prevalence. Thus, the relationship between the genotype-specific conditional probabilities and disease prevalence can be represented by the following formula:

P(D|AA)*P(AA)+P(D|AG)*P(AG)+P(D|GG)*P(GG)= Pd where P(G) is the frequency of genotype G in the population, P(D1G) is the probability of developing a disease given the genotype G, and Pd is the disease prevalence or the average population probability of disease.

A population-adjusted odds ratio, or an individual's genetic risk relative to the average population, can then be computed given the above formulas by solving the following system of equations:

$$P(AG|Ave) = \frac{\frac{P(D|AG)}{1-P(D|AG)}}{\frac{P_d}{1-P_d}}$$

$$P(GG|Ave) = \frac{\frac{P(D|GG)}{1-P(D|GG)}}{\frac{P_d}{1-P_d}}$$

$$P(AA|Ave) = \frac{\frac{P(AA|GG)}{1-P(AA|GG)}}{\frac{P_d}{1-P_d}}$$

where Pd is the average probability of developing the disease in the given population, and P(D|G) is the probability of developing the disease given the genotype G.

Furthermore, to get a better estimate of the genetic risk at certain loci, certain embodiments also compute the OR for haplotypes, or genetic variants in close chromosomal proximity to one another whose alleles are inherited together more often than would be expected by chance. In certain instances of genetic association, a single genetic variant alone may not be associated with a phenotype of interest, but rather a specific combination of nearby variants, or haplotypes, may be associated with the phenotype. In such instances, the haplotype alleles (combinations of single variant alleles) can be used to compute odds ratios and help derive an individual's genetic risk for a phenotype of interest.

FIG. 3, similar to FIG. 2, is an exemplary data structure for a haplotype OR computation. In FIG. 3, however, the columns are for the haplotype allele, odds ratio, frequency in cases, and frequency in controls.

Using a data structure like the one in FIG. 3, and assuming that the haplotype allele with the largest frequency in the control sample is the reference allele, certain embodiments compute the OR for an allele relative to the reference allele using the following formulas:

| Haplotype allele | Odds ratio | Confidence interval | Number cases | Number controls |
| --- | --- | --- | --- | --- |
| A | $OR_A = 1$ | NA | $N_A = p_a * 2N$ | $M_A = p_u * 2M$ |
| B | $OR_B = q_a p_u / p_a q_u$ | $\exp(\ln OR_B +/- 1.96 * \sqrt{(1/N_A + 1/M_A + 1/N_B + 1/M_B)})$ | $N_B = q_a * 2N$ | $M_B = q_u * 2M$ |
| C | $OR_C = r_a p_u / p_a r_u$ | $\exp(\ln OR_C +/- 1.96 * \sqrt{(1/N_A + 1/M_A + 1/N_C + 1/M_C)})$ | $N_C = r_a * 2N$ | $M_C = r_u * 2M$ | where Nx is an estimate of the number of cases with allele x and Mx is an estimate of the number of controls with allele x.

The genotype OR, which quantifies a person's risk of developing a certain disease, can simply be the product of the allelic OR for that genotype (for example, OR{A/B}=OR {A}*OR{B}).

Similar to SNP-based ORs, certain embodiments can compute the adjusted OR of a haplotypic genotype using the above equation used for SNPs. However, since there are often no haplotypic genotype frequencies in the source data, certain embodiments can estimate the haplotype genotype frequencies assuming Hardy-Weinberg equilibrium from the haplotypic allele frequencies in control. Certain embodiments can then use the following formula to compute the frequency:

| genotype | frequency in controls |
| --- | --- |
| A/A | $f(A/A)_u = p_u^2$ |
| B/B | $f(B/B)_u = q_u^2$ |
| C/C | $f(C/C)_u = r_u^2$ |
| A/B | $f(A/B)_u = 2p_u q_u$ |
| A/C | $f(A/C)_u = 2p_u r_u$ |
| B/C | $f(B/C)_u = 2q_u q_u$ |

Once the frequencies are computed, the prevalence or risk of disease in the average population can be computed using the following equation:

$$P(D|AA)*P(AA)+P(D|AG)*P(AG)+P(D|GG)*P(GG)=Pd$$

Figure 4:
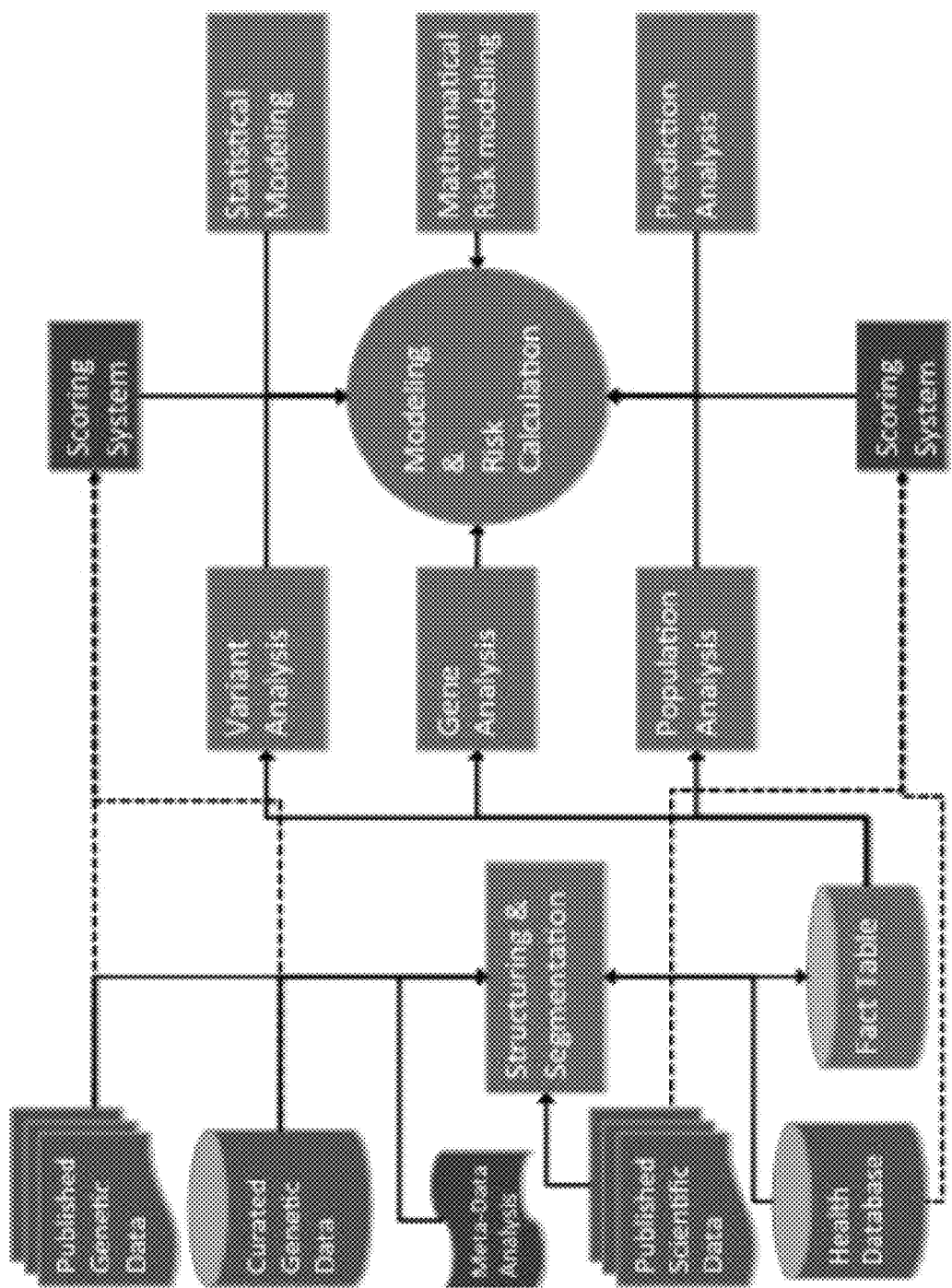
FIG. 4 is a schematic illustration showing a flowchart of an overall system flow according to certain embodiments.

FIG. 4 is a schematic illustration showing a flowchart of the overall system flow. As shown in FIG. 4, and as discussed elsewhere herein, various inputs such as published genetic data, curated genetic data, published scientific data, and a health database can be analyzed for meta-data, placed into a fact table, and scored. Moreover, variant analysis, gene analysis, population analysis, prediction analysis, mathematical risk modeling, and statistical modeling can be applied to the data. Finally, modeling and risk calculation can be performed on the analyzed and processed data.

The risk engine can combine genetics, environmental and behavioral risks into one uniform or homogeneous measure of the risk of developing a specific phenotype.

The risk engine can also calculate whether a particular factor increases or decreases an individual's chances of developing a specific phenotype. Thus, the risk engine can determine whether a particular factor is a risk factor or a protective factor for a given individual.

Variant scoring can be used to assess which variant, out of all the studied genetic variants, best and independently predicts an individual's genetic risk of developing a specific phenotype while minimizing over-estimation.

Environmental factor scoring can be used to assess which factor, out of all the studied environmental and behavioral risk factors, best and independently predicts an individual's non-genetic risk of developing a specific phenotype while minimizing over-estimation.

Lifetime risk can refer to the odds of developing a specific phenotype in a given individual's lifetime relative to baseline (environmental and behavioral risk factors) or average (genetic risk).

The baseline can be defined as a healthy, normal version of a given individual, as defined by conventional medical parameters. In other words, the baseline can be defined as a hypothetical individual of a given gender and ethnicity who harbors no environmental/behavioral or genetic risk factors. For genetic risk, an individual's genetic risk can be compared to the average genetic risk of the ethnicity/population to which the individual belongs.

An achievable risk can represent the extent to which a person can improve his/her health by maximally reducing all lifestyle risk factors within his/her control.

Family history can be used as a risk factor for developing a phenotype, for example if a first- or second-degree relative has the given phenotype. Diet and physical activity can be considered in scoring and risk assessment of lifestyle choices and behavioral activities on developing a specific phenotype.

Figure 5:
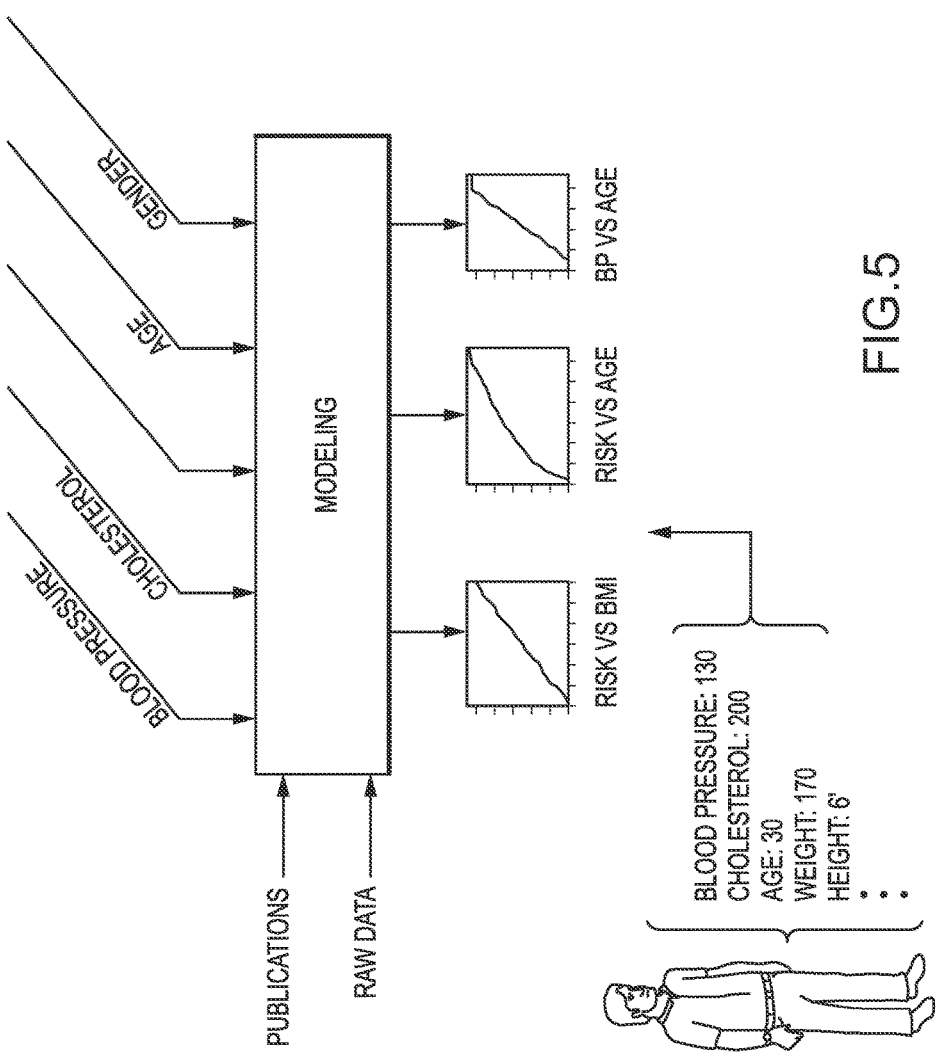
FIG. 5 is a schematic illustration showing a system overview from a high level of an environmental risk engine according to certain embodiments.

FIG. 5 is a schematic illustration showing a system overview from a high level of an environmental risk engine. As shown in FIG. 5, modeling can provide outputs such as risk vs. BMI, risk vs. age, and blood pressure (BP) vs. age, based on inputs of publications and raw data, as well as based on personalized inputs, such as a particular person's blood pressure, cholesterol, age, and gender, among other things. In the particular illustration, the person has a systolic blood pressure of 130, cholesterol of 200, age 30, weight 170 pounds, and height of six feet.

An environmental risk engine can take various lifestyle and other environmental factors into consideration. Lifestyle and environment can be divided into two major categories. A first category includes the factors that are related to an individual's environment and depend on the individual's style of living, which may be under the individual's control. These can be characterized as modifiable. Blood pressure, cholesterol, diet, and physical activity are examples of factors in this category. A second category includes factors that are related to an individual's environment or history that cannot be changed. These non-modifiable risk factors can include age, gender, ethnicity, and past smoking history, for example.

Sources of data for the environmental risk engine can include scientific articles and raw data. For the phenotypes of interest, publications and journals can be researched utilizing online or other search engines. An aspect of this process can be to determine whether an article is scientifically sound and can be considered for modeling purposes.

Various criteria can be used to determine acceptance of a scientific publication. The title of the paper can be evaluated to determine whether the paper is related to a phenotype and/or to a risk factor of interest. The journal in which the paper is published can be considered as an indicator of the study's scientific rigor and the acceptance of the results in the scientific community. This criterion can be implemented by creating a list of reputable journals and favoring studies published in these journals. The publication date can be limited to publications within the last 10-15 years. Seminal studies that are older than 15 years old but are repeatedly referenced by recent studies may also be accepted.

Various study types can be accepted. Prospective cohort studies can include studies that follow a healthy population (without the phenotype of interest) over a specific period of time and record the number of subjects who acquire the phenotype during this period along with a variety of environmental factors. Such a study may allow determining the causative risk factors as opposed to those merely correlated with the phenotype.

Case-control studies can include two groups of subjects, one comprising individuals with the phenotype, the other comprising individuals without the phenotype. In such a study, the two groups can be compared to determine the risk factors correlated with the phenotype.

Retrospective studies can consider a population of individuals with the phenotype and can retrospectively record the timing when these individuals first developed the phenotype. Such studies may permit determining the risk factors correlated with the phenotype.

Cross-sectional studies can consider the whole, or a subsection, of a population at a specific time to determine the risk factors correlated with the phenotype.

Diagnostic tools/criteria can be a factor in considering a paper. For example, the paper can be considered acceptable when the paper uses reputable diagnostic tools or criteria that have been validated by medical professionals.

The paper's acceptance can also depend on the makeup of the study subjects. For example, in the case of an acceptable study, the gender is mixed, unless the phenotype is gender-specific and individuals are excluded because of death only. The study may be required to have a sufficiently large sample size, which may depend on the study type: for a prospective study, the sample size minimum can be 100 individuals; for a case-control study, the sample size minimum can be 250 individuals in cases and in controls; for a retrospective study, the sample size minimum can be 500 individuals; and for a cross-sectional study, the sample size minimum can be 500 individuals.

As mentioned above, the exclusion criteria of a study can rigidly be only for death. Alternatively, the study exclusion criteria can be because of participants' non-responses or death. Studies that excluded data to improve the significance of their results can be rejected.

The kind and quality of statistical analysis provided in the paper can also be used as acceptance criteria. Statistical results presented in terms of odds ratios can be favored over beta and/or mean-value analyses. Studies with beta-analysis or mean values can be considered replications to further validate a specific risk factor.

Papers may be accepted when the results are significant. For example, the papers may be accepted when the confidence intervals do not span 1.0 and when the P values are statistically significant.

Once an article is accepted to be used in modeling the association of a risk factor with a phenotype, the article's results can be extracted in a contingency table.

FIG. 6 is a schematic illustration showing a sample table extracted from an article to be used in modeling the association of a risk factor with a phenotype. As shown in FIG. 6, the table includes various values of blood pressure, associated odds ratios, and associated confidence intervals.

In order to obtain an odds ratios for every possible value of a risk factor, the following steps can be used: first, data points from the article can be used to fit a linear model or sometimes piece-wise linear depending on the data; and second, the fitted linear model can be used to interpolate and find odds ratios for all the points within that range.

Figure 7:
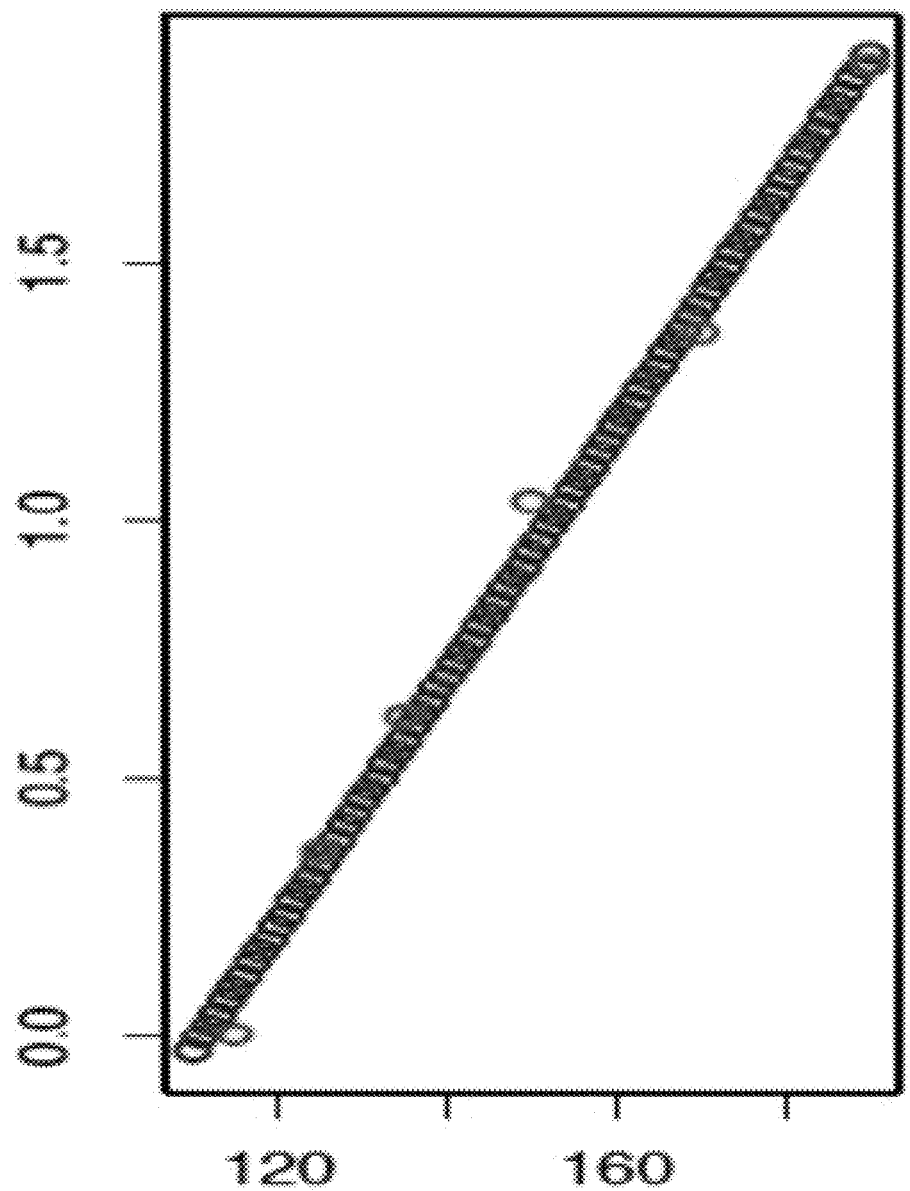
FIG. 7 is a schematic illustration showing a linearly interpolated data, in accordance with certain embodiments.

FIG. 7 is a schematic illustration showing a linearly interpolated data, wherein the data points are from an accepted article to fit the linear model and wherein the fitted linear model is used to interpolate and find odds ratios for all points within that range. As shown in FIG. 7, a line can be generated based on several data points.

As mentioned above, raw data can also be used. Public health related databases can be a primary data source for data analysis. Data can be downloaded from sources like the CDC (e.g., NHANES), and statistical analyses can be performed to identify significant risk factors.

FIG. 8 is a schematic illustration showing a sample result of statistical analysis in the R programming language. The illustration is just one example of possible outcomes from statistical analysis, but illustrates the deviance residuals, coefficients, among other statistical measures, that can be computed.

The National Health and Nutrition Examination Survey (NHANES) is a national survey conducted across counties in the United States by the Centers for Disease Control and Prevention (CDC). Every two years, data from approximately 10,000 new individuals across different ethnic, age and socioeconomic groups are collected through extensive questionnaires, physical examinations and laboratory tests. This data is then sorted into five different categories: demographic data, which contains information about the age, ethnicity and gender about the sample; dietary information, which contains dietary habits for these individuals; examination data, which contains the results from the physical examinations conducted by medical doctors; laboratory information, which contains the results from blood tests and urine analysis; and questionnaires, which contain the results from the interviews conducted by representatives of the CDC. All of the results from the survey are then published on the CDC website under the NHANES section, where any researcher can use the publicly available data.

Figure 9:
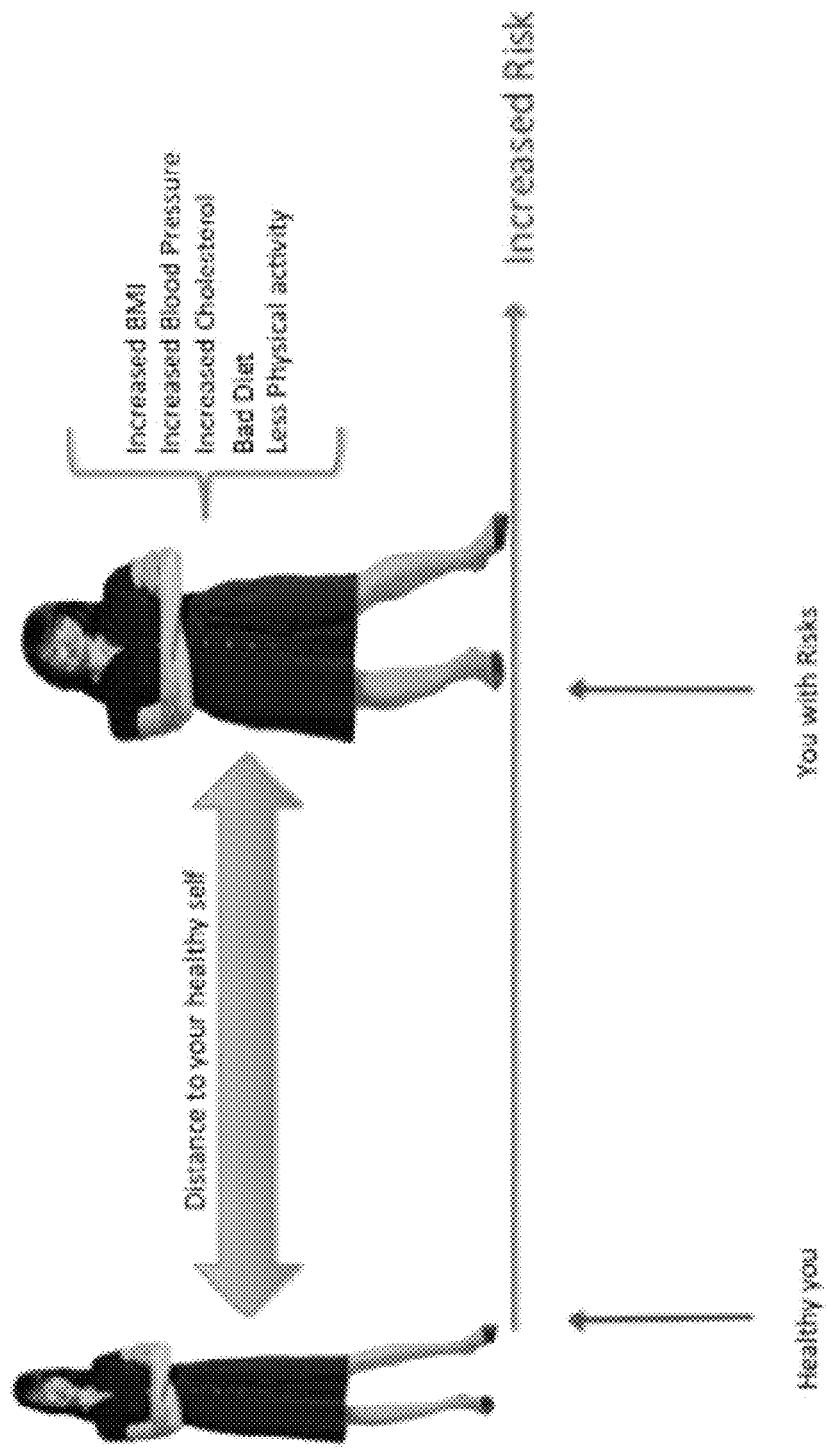
FIG. 9 is a schematic illustration showing personalization of an engine according to certain embodiments.

FIG. 9 is a schematic illustration showing the personalization of the engine. More specifically, an individual's risk can be computed and reported relative to an otherwise healthy individual of the same age, gender and ethnicity. That is, an individual can be compared to the healthiest version of himself/herself, defined as a healthy individual of the same age, gender and ethnicity who possesses no risk factors of disease (aside from those inherent to age, gender and ethnicity). The system reports and visualizes the difference between an individual's current disease risk and his/her disease risk were he/she perfectly healthy.

FIG. 9 shows an example of "healthy you" on the left and an example of "you with risks" on the right. The risks identified include increased BMI, increased blood pressure, increased cholesterol, bad diet, and less physical activity. The "healthy you" is shown separated by a distance from the "you with risks", based on the amount of increased risk between the "healthy you" on the left and the "you with risks" on the right.

Personalization can be applied by the environmental risk engine. With respect to genetics, each individual's genome is unique, so a personalized genetic risk calculation can be performed and compared to the average genetic risk of a given population. With respect to environmental factors, each individual can have elevated or decreased risk relative to a healthy individual of the same age, gender and ethnicity. That is, an individual can be compared to a healthy version of the individual, where the individual's risk factors are removed aside from his/her age, gender and ethnicity. The individual, thus, is not compared to a population average. Rather, certain embodiments can tell the individual the extent to which he/she deviates from the healthiest version of the individual.

Figure 10:
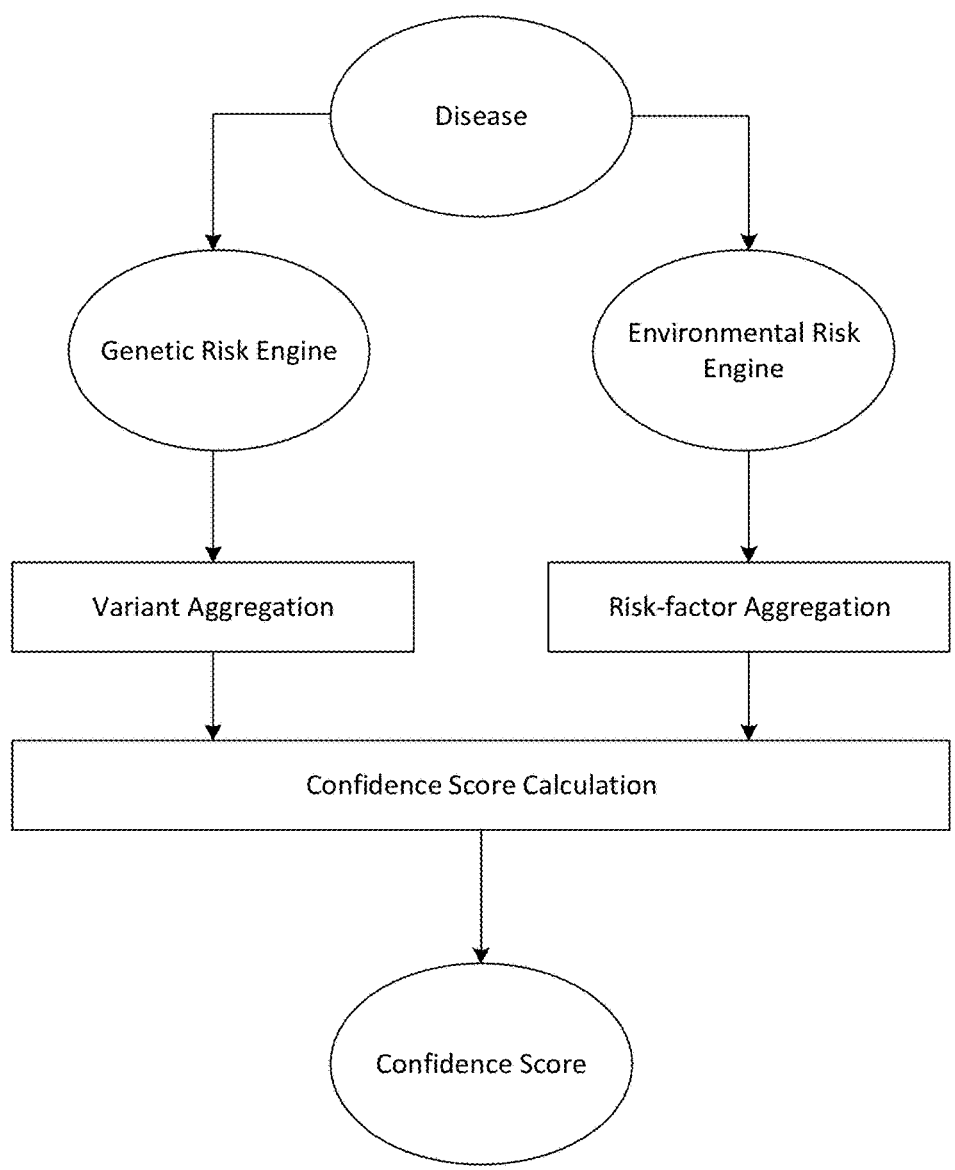
FIG. 10 is a schematic illustration showing a flowchart of the confidence associated with a prediction model, according to certain embodiments.

FIG. 10 is a schematic illustration showing a flowchart of the process by which confidence associated with each disease prediction model is assigned. In particular, the confidence measure for each disease model integrates the confidence of the genetic risk engine as well as the environmental risk engine. Confidence scores can be based on how well supported the risk factors for each engine are based on the available scientific evidence.

Thus, as shown in FIG. 10, for a given disease, there can be an analysis both by a genetic risk engine and an environmental risk engine. In the case of the genetic risk engine there can be variant aggregation and in the case of the environmental risk engine there can be risk-factor aggregation.

A confidence score can be calculated on the aggregated output of the engines. Finally, a system-specific confidence measure can be output for the disease based on both genetic and environmental risk factors used in the disease model. For each risk factor, the confidence score can take into account the scientific evidence supporting the association, including extent of association replication, study types, sample sizes, statistical models employed, and the strengths of the reported associations.

There can be confidence associated with every prediction model. The specific confidence of certain embodiments can integrate the confidence of a genetic risk engine as well as an environmental risk engine.

Figure 11:
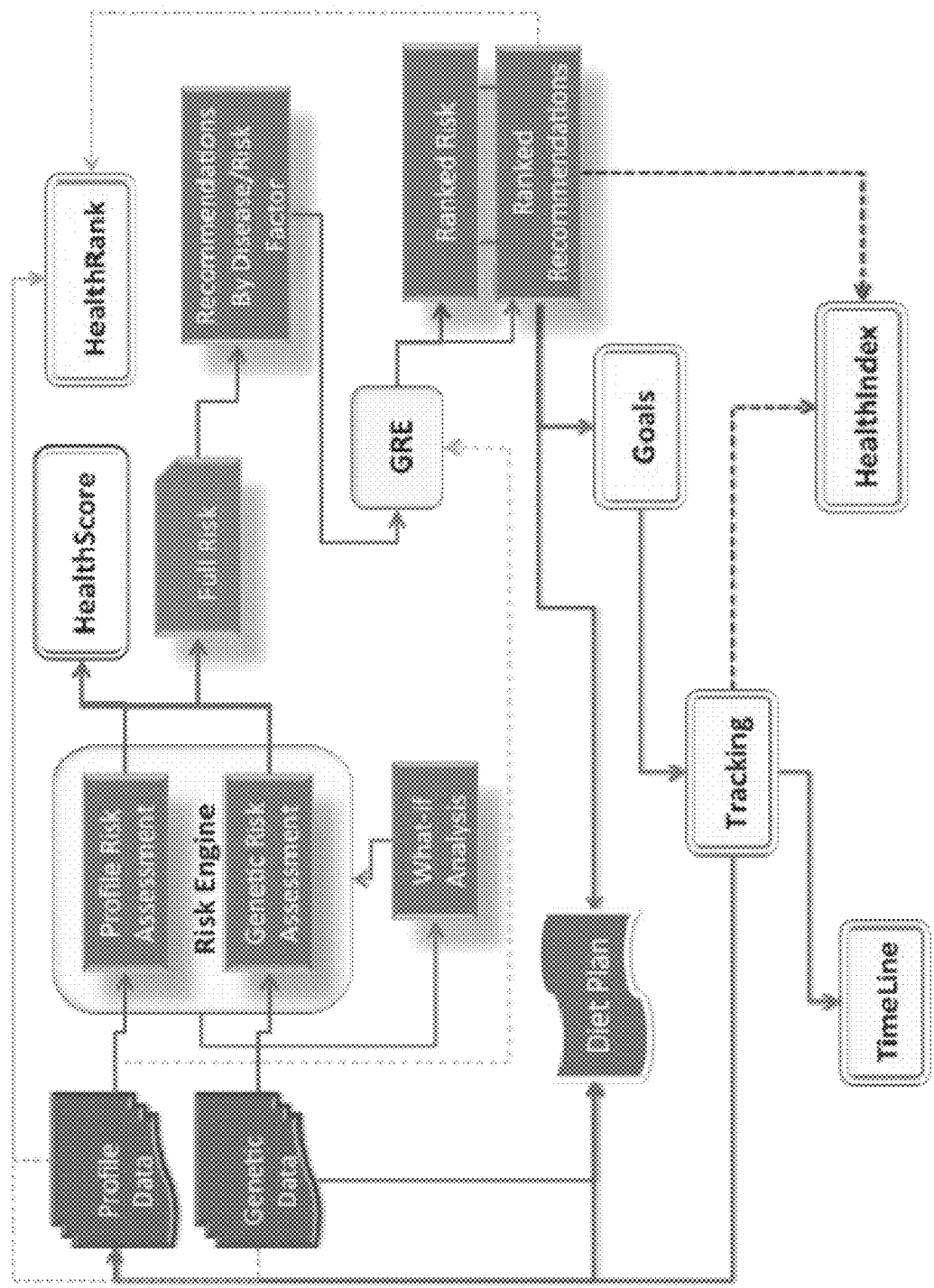
FIG. 11 is a schematic illustration showing a flowchart of overall system interactions according to certain embodiments.

FIG. 11 is a schematic illustration showing a flowchart of the overall system interactions. As shown in FIG. 11, profile data can be data entered by a user via a graphical user interface (GUI). A subset of the data, such as laboratory results, can also be entered by physicians. Parts of data may come from third-party applications, such as automatic weight scales, which may be downloaded wirelessly via Wi-Fi or Bluetooth.

Genetic data for the engine can originate from gene or genome-wide genotyping or sequencing, and the subsequent analysis of said data, as mentioned above. An environmental risk engine can compute a risk assessment based on an individual's environmental data. Likewise, a genetic risk engine can compute risk assessment based on genetic data.

A what-if engine can provide an interactive way of exploring risk factors and demonstrating how changing such parameters affects an individual's current and lifetime disease risks.

A recommendation engine can use an individual's disease risk assessments and other environmental or genetic data to provide recommendations for controlling modifiable risks. The recommendation engine output can be provided per disease and per risk factor as well as aggregated across diseases and/or risk factors.

A global recommendation engine (GRE) can aggregate and rank all the recommendations to a single list. The GRE can also convert the risks to rules. The rules can then be used for further processing.

The recommendations can include a diet plan. For example, based on the specific environmental or genetic components of an individual's disease risks, the system can generate a recommended diet plan.

The recommendations can also include action goals. The user of the system can elect to take action based on the recommendations. Moreover, the system can provide tracking of an individual's progress toward achieving action goals. Elements in the profile and goals can be tracked over multiple lab test results, exercise patterns, actual diet, and so forth. The user can chart the tracked items to evaluate his/her progress and areas for improvement. For example, diet can be tracked against high-density lipoprotein (HDL) or exercise can be tracked against triglycerides (TGL).

A health score as used herein can refer to a numerical representation of the state of a member's health. A health index as used herein can be a function of the recommendation and tracking, as will be discussed below. A health rank as used herein can take the profile, genetics, and recommendations into consideration, as will be discussed in more detail below.

A risk assessment system can compute risk for an individual based on multiple data sources: the user-generated and physician-generated data from the individual's profile; and the genetic data from genotyping or genome sequencing. The risk modeling can take into account demographics, lifestyle factors, and clinical and laboratory measurements, among other factors. The risk modeling can also take into account multiple genetic risk factors, including but not limited to single-nucleotide polymorphisms (SNPs), copy-number variations (CNVs), and small insertions and deletions (indels). The risk factors can be simple or derived risk factors. The risk algorithm engine can employ statistical models constructed from the above factors using standard techniques of statistical learning. Raw risk factor input values can be translated into discrete normalized risk values by the use of lookup tables that transform non-discrete inputs into normalized and discrete values. The output of the risk assessment system can be a list of risks/diseases and a list of recommendations for each risk/disease. The recommendations can include personalized recommendations for an individual's behaviors, diet, physical activity, and use of medications, supplements, and nutrients.

FIG. 11 is a schematic illustration showing a flowchart of the overall system interactions. The GRE system can evaluate disease risk assessments generated by the risk engine to produce global recommendations. While the risk engines and the what-if engines can look at risks in the context of one disease/risk factor, GRE can take integrate the risks and risk factors of all diseases globally. Features of the GRE can include aggregation, ranking, and providing granular, meaningful recommendations geared toward changing the user's behavior. For example, a diet plan module can provided personalized, detailed recommendations for how the user can improve his or her diet.

The GRE can be a precursor to the following: a health index, which can be a measure of how the Things To Do (TTD), derived from the GRE, are tracked over time, as discussed below; a tracking and social engagement module; a timeline module for graph and overlay; and health rank and reader personalization, based on the GRE, risks and other things.

The functions of the GRE can include the following: capture complex relationships between the risks/diseases; capture the various risk and recommendation elements in the form of multiple rules so that they can be reconciled; process elements having a set of quantifiable metrics for the goals so that they can be measured, graphed, and tracked; capture weights of each risk and recommendation; reconcile and rank the risks; reconcile and rank the recommendations; and rank recommendations and trim them to a set of concrete, high-impact lifestyle recommendations. The trimmed set may have, for example, a maximum of seven or so recommendations.

Ranking can include voting-based federation, cost function-based metrics calculation, and positive and negative voting with weights, priorities, and veto. The ranking can also include assigning a strength or weight to each factor and then deriving recommendation strength based on the relative strengths of risk factors.

The engine can provide contextualized, aggregated, syndicated, analytics-based, and multi-dimensional results. The results can be contextualized in terms of the current state of the individual's profile, including information about an individual's demographics, behaviors, environment, and genetics. The results can be aggregated across risks and disease. The results can be syndicated in terms of ranking based on voting from multiple heterogeneous concepts, sources, and domains. Moreover, the results can be based on analytics derived from the datasets. The results can be multi-dimensional in terms of considering many factors and sub-factors. Certain embodiments can provide the ability to select Things To Do (TTD) from ranked recommendations for a goal list. The TTD can be provided in conjunction with consultation with a physician and, in the case of diet-related goals, a dietician.

Figure 12:
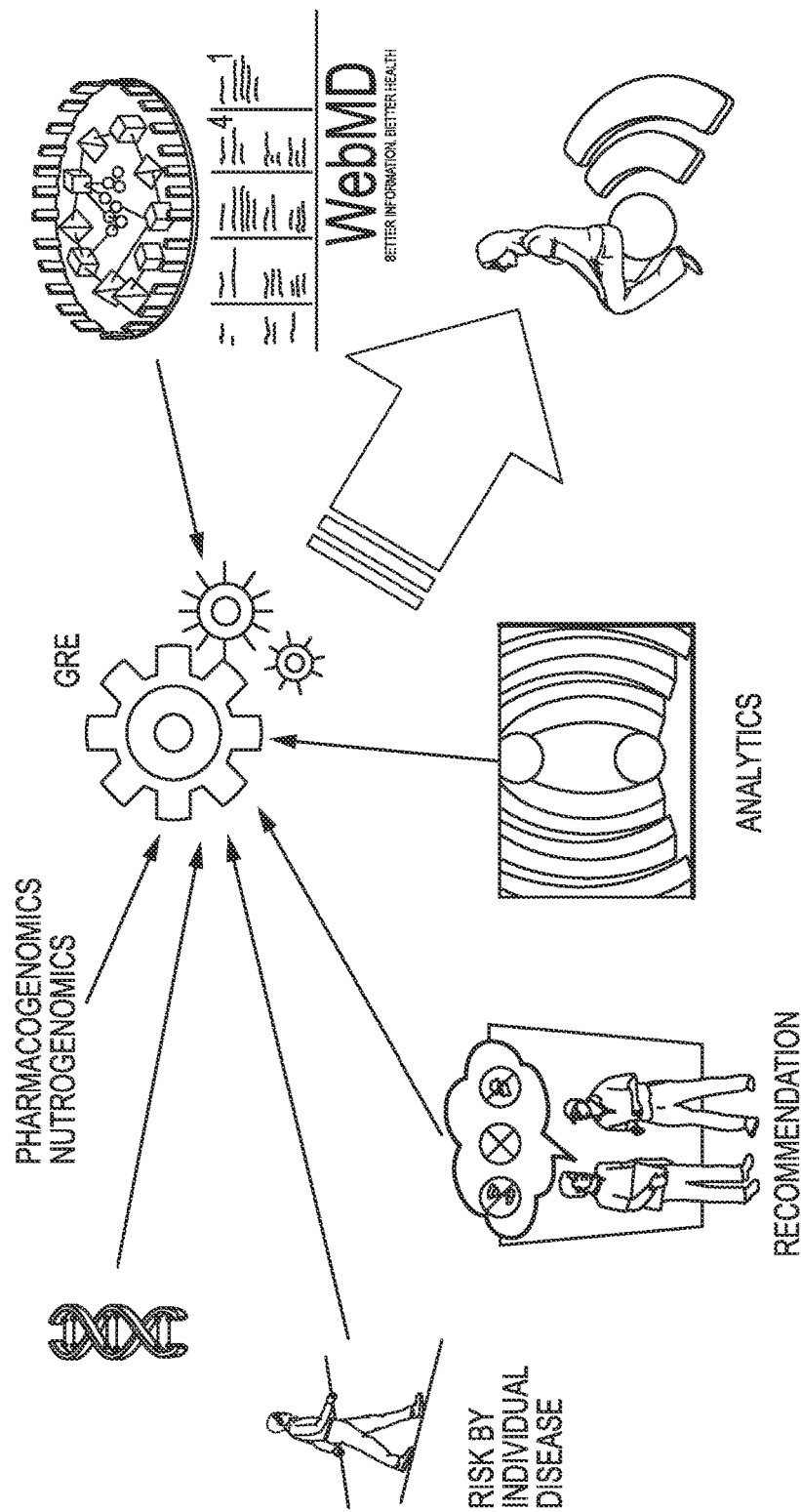
FIG. 12 is a schematic illustration showing a flowchart of a Global Recommendation Engine (GRE) according to certain embodiments.

FIG. 12 is a schematic illustration showing a flowchart of the GRE. The GRE can have a variety of inputs. The inputs of the GRE can include the following: output from one or more risk engines, including risks and recommendations by disease; phenotypes; genotypes; cost function(s) for risks, diseases, genotypes and phenotypes; risk/disease probabilities; fact graphs for diet; fact graphs for activity; fact graphs for pharmacology; and fact graphs for nutrition.

The GRE processing can follow the following sequence. This sequence is just an example, and other sequences of processing are also permitted. First, the GRE can consolidate, syndicate, and aggregate recommendations to an ordered list, based on one or more cost functions. Then, the GRE can order recommendations by risk magnitude based on genetic and environmental risk factors. Next, the GRE can order recommendations based on probability of occurrence.

Subsequently, the GRE can apply prioritized overlays. For example, if an individual's genotype predicts a specific predisposition, the GRE can first apply an overlay related to that predisposition before other types of recommendations. Then, the GRE can apply the other overlays.

Next, the GRE can derive the ordered risks. Then, the GRE can aggregate and consolidate the recommendations for the risks, keeping the risk ranking. After that, the GRE can rank and order the recommendations.

Furthermore, the GRE can keep track of the reasoning chain for explanation to the user, drill down specificity, or debugging. Finally, the GRE can keep track of the history and origin of the risks and recommendation for tracking and explanation.

Figure 13:
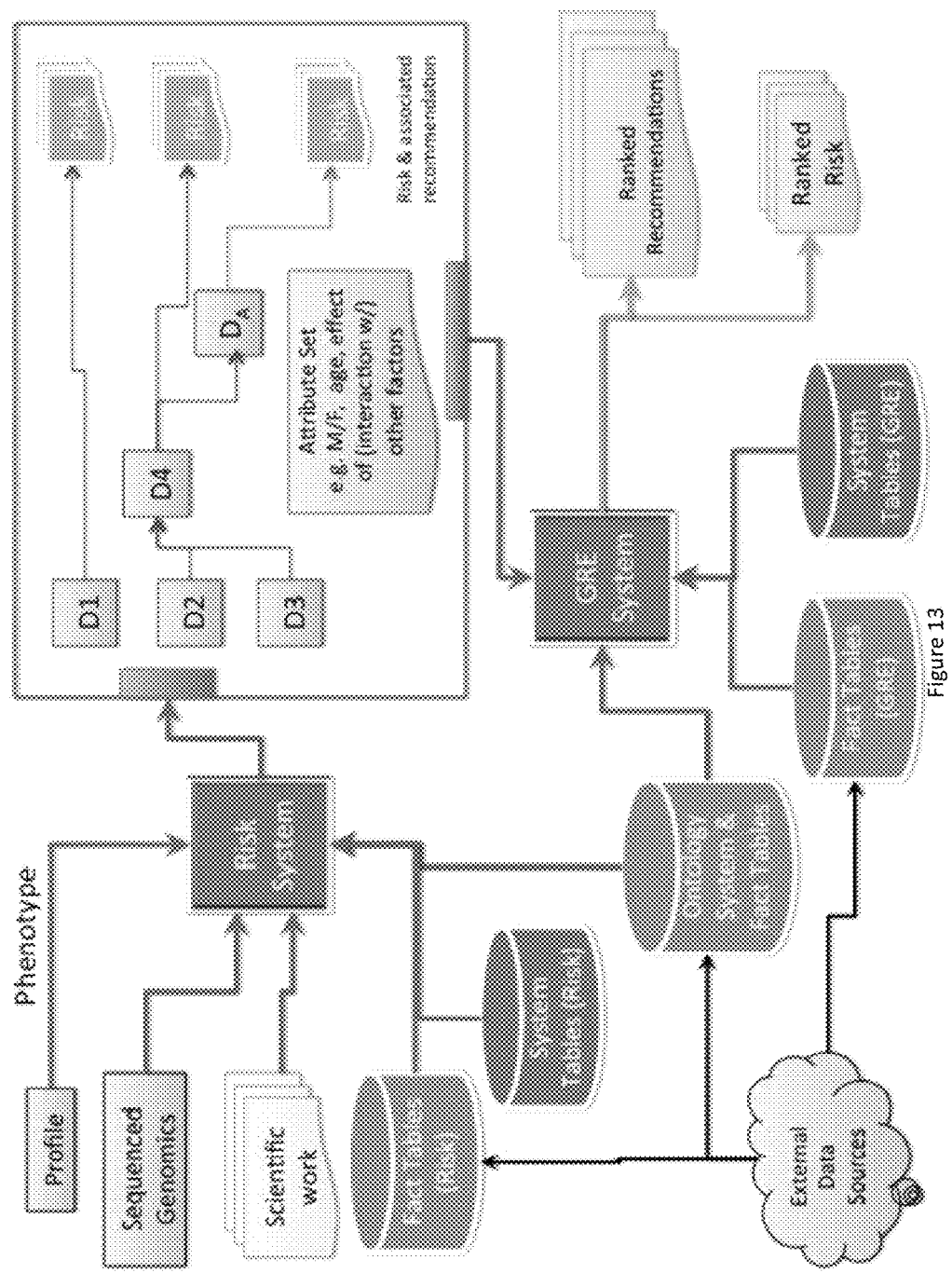
FIG. 13 is a schematic illustration showing a flowchart of risk and GRE system flow according to certain embodiments.

FIG. 13 is a schematic illustration showing a flowchart of a risk and GRE system flow. Risk and recommendation syndication can involve various procedures. The following procedures are provided in a sequence, but the sequence can be varied. First, the risk and recommendation syndication can include converting the risk and recommendations (by risk/disease) to normalized quantifiable factors. The coded normalized factors do not need to all be numbers. There can be flexibility to capture the essence of a factor, rather than force fitting the factor into a single coding scheme.

The coding scheme can be, for example, nominal, ordinal, interval or ratio. Nominal schemes can be categorical, such as vegetable types or activity types. While they possess distinctiveness, they need not have any particular order and they could be hierarchical.

Ordinal schemes can include ranking (e.g., high, medium, and low, or 1 to 10). There is an order but one cannot add them or divide them. By contrast, in interval schemes order, ranking and addition may be possible. Difference may be meaningful but ratio may not be. Finally, in a ratio scheme normal numbers may be used, with all their properties.

Reason for coding and normalization can vary, but can include ranking globally instead of by risk or disease. Other reasons for coding and normalization are also permitted.

Next, the system can assign strength overlays to the risk factors. The strength overlays can be based on user preference, the magnitude of the user's risk for a given risk factor, as well as the baseline probability of the risks themselves. Mathematically, the process can include the life quality of the risks such as measures of survivability or quality of life. The strength can also incorporate an intra-genetic dimension of the risk.

After that, the system can order the coded factors to a raw global list. The ordering can depend on the type. The system can collect all nominal factors into the categories, order ordinal factors, and rank and list the interval and ratio factors. Backward chaining can be employed if the factors have complex dependency.

Then, the system can apply genomic cost functions, for example, on risk factors and recommendations. Each of the major types of factors, can have its own functions based on the genotypes and phenotypes. The major types can include, for example, diet, activity, pharmacology, and nutrition.

This application of genomic cost functions can be a product operation on factors versus the fact tables versus the cost functions. For example, if the genetic makeup says LeafyVegetable=−10, then a product of the associated graphs would take out the leafy vegetable node. Alternatively, if the genetic makeup says running=100 or even running=best, then running would show up high in the activity recommendation. Running=100 and running=best are two different normalizations, 100 being interval and "best" being ordinal.

Next, the system can apply probabilistic occurrences of diseases to adjust the weight of certain recommendations. For example, an individual might have an elevated relative risk for a particular disease; however, if the probability of the disease occurring in the general population (i.e., the prevalence) is low, then the individual's absolute risk for the given disease remains small. In such cases, the recommendations derived from that disease risk model may be assigned a lower rank. Sophisticated Bayesian models can be applied in this procedure.

Subsequently, the system can apply overlays iteratively based on their respective priority. For example, an overlay can be based on user preference. Another overlay can be based on gender. Thus, the system can apply a set of overlays that alter the ranking and the intensity of the disease risks and thus the priority of the various recommendations.

After that, the system can derive a single list of ranked risks and recommendations. Some recommendations may conflict each other. These conflicts can be resolved by a voting scheme. Some recommendations may be additive. There may, however, be limits. For example, the system can be configured to avoid recommending consuming excessive amounts of vitamins that improve health when consumed at an appropriate dose. How the conflicting and complementary factors are handled may depend on the type of factors involved.

The system can then provide the final list as the global disease risk and recommendation. The list can contain the ranks of the disease risks and recommendations as well as their relative strengths. The list can be processed appropriately by different interfaces. For example, a health ranking system can prioritize and rank the information content incorporating the relative ranking of the GRE.

Various other options are possible. An external application store interface may have a threshold and may send only the items in the list with a higher value than the threshold. The goals screen may show the list in a decreasing order of rank. The screen may also show the reasoning chain and provide capability for drilldown specificity. The TTD screen may show only the top seven items and may even trim the list to the seven items or to fewer than seven items, based on thresholds.

Finally, the system can store the reasoning chain paths and intermediate results in a database. This database can be used for drill down specificity or debugging.

Various considerations can be made. For example, the recommendations could be ranked based on impact factor or risk factor odds, and prevalence of a risk factor. The recommendations can follow the ranking of the risk factors. If more than one risk factor votes up a recommendation, the recommendation can be assigned a higher rank. A recommendation can be voted up by one risk factor and down by another. Then, the voting weight multiplied by the rank of the risk can decide the rank of recommendation. There can be negative recommendations, such as avoiding eating meat or avoiding smoking. Overlays can veto a recommendation.

Because recommendations are ranked, they can be independent of categorization like diet, activity, pharmacology, and nutrition. The assignment of ranks and cost function can be validated with physicians. User preferences can be obtained by querying a user and can be used to add weight to certain recommendations.

Figure 14:
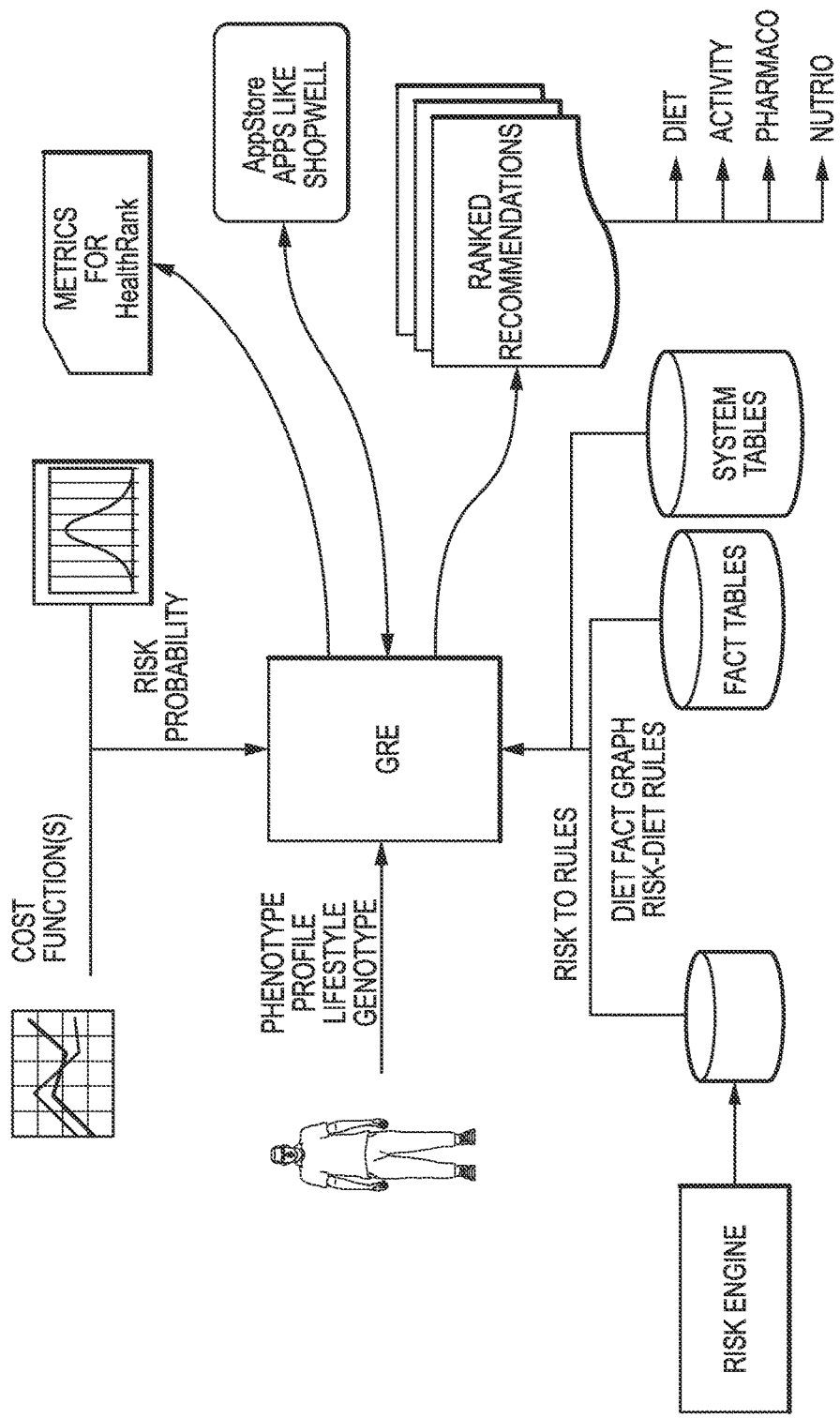
FIG. 14 is a schematic illustration showing a flowchart of a GRE flow, at a very high level, according to certain embodiments.

FIG. 14 is a schematic illustration showing a flowchart of the GRE flow, at a very high level. FIG. 14 illustrates the GRE accepting various genotype/phenotype inputs, together with various cost function(s) and risk probability information and outputting metrics for a ranking system, data for applications, and ranked recommendations, based on risk rules.

Figure 15:
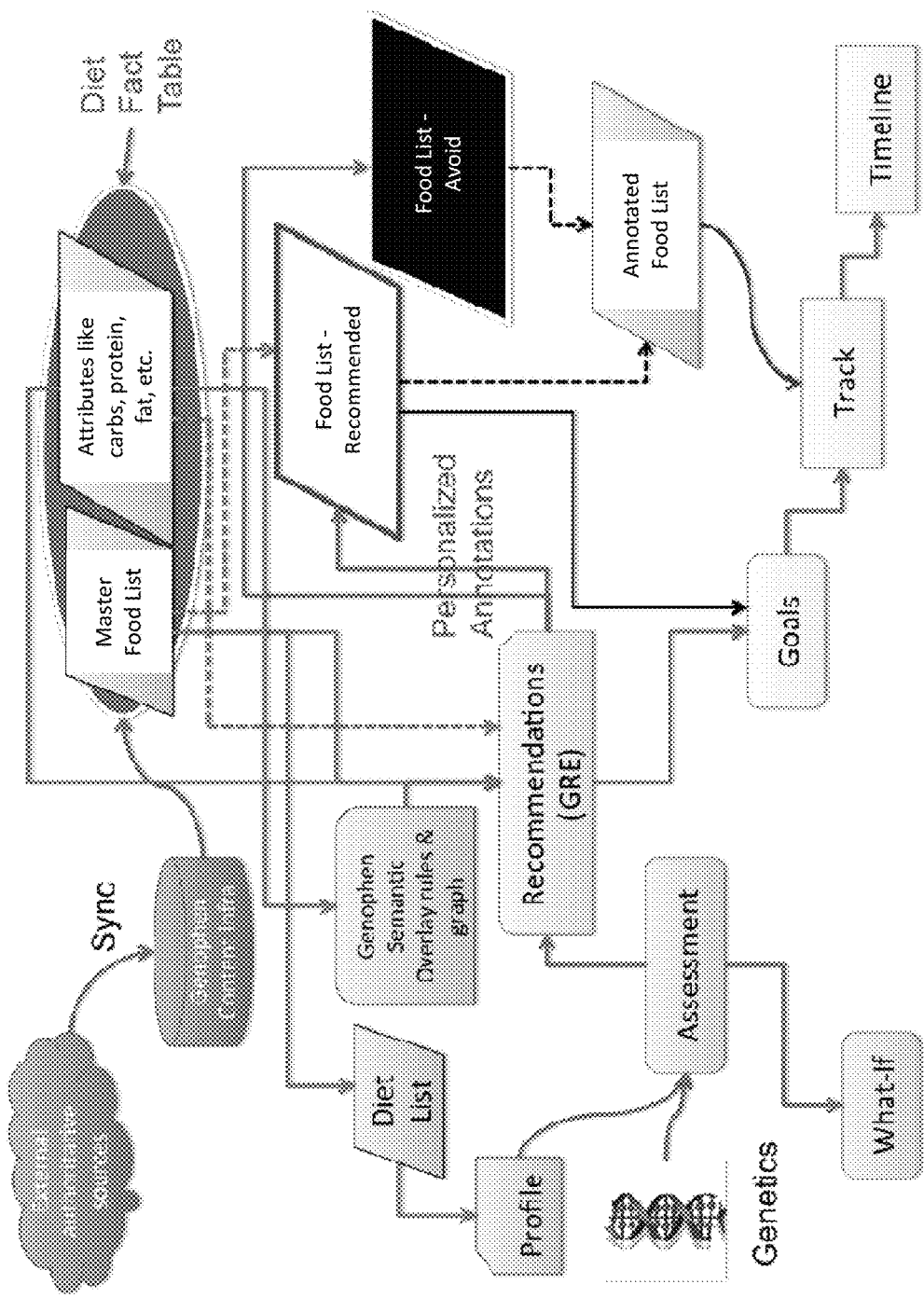
FIG. 15 is a schematic illustration showing a flowchart of the flow and processing of recommendation through the system according to certain embodiments.

FIG. 15 is a schematic illustration showing a flowchart of the flow and processing of recommendations through the system. The recommendation processing flow can involve a process having a sequence. The sequence provided below is illustrative of one approach, but the steps of the sequence can be performed in other orders, if desired.

First, a comprehensive diet list can be kept in synchronization with external authoritative sources, as a part of the health ranking content management and the list is created in a database. This can be the master list used in instances where the system needs a list of food items, such as the detailed diet section of an individual's profile. The list can also have associated health data about a food item, such as carbohydrate, fat, and protein content.

The diet fact table can be populated from a content infrastructure. System-specific semantic overlay rules and graph can contain the diet rules for various risk factors, in terms of food items that are recommended to eat or avoid.

As already mentioned elsewhere, the assessment engine can calculate the risk factors based on genetics, environmental and behavioral attributes. Based on the risks, the recommendation engine can output a ranked list of recommendations and goals.

The recommendation engine can annotate the master food list and output a list of recommended food items (Food List—Recommended) and a list of food items to avoid (Food List—Avoid). The inputs for this step can be the diet fact table, the semantic overlay and the risks and recommendations. Triangulating among these data sets, the recommended list can be made up of items that are good for an individual and the avoid list can be items that are not good for an individual. The GRE-derived goals can display food items from the recommended list (Food List—Recommended) to encourage a user to incorporate such food items into his/her diet.

The tracking feature can enable a user to add items that the he or she has consumed. Here, the entire master list (Annotated Food List) can be shown, along with annotations from the recommended/avoid lists to enforce and remind the user of the GRE-derived goals.

Because of the cyclical relationship between assessment and risk calculation and the goals, there can be a semantic process as described herein.

Figure 16:
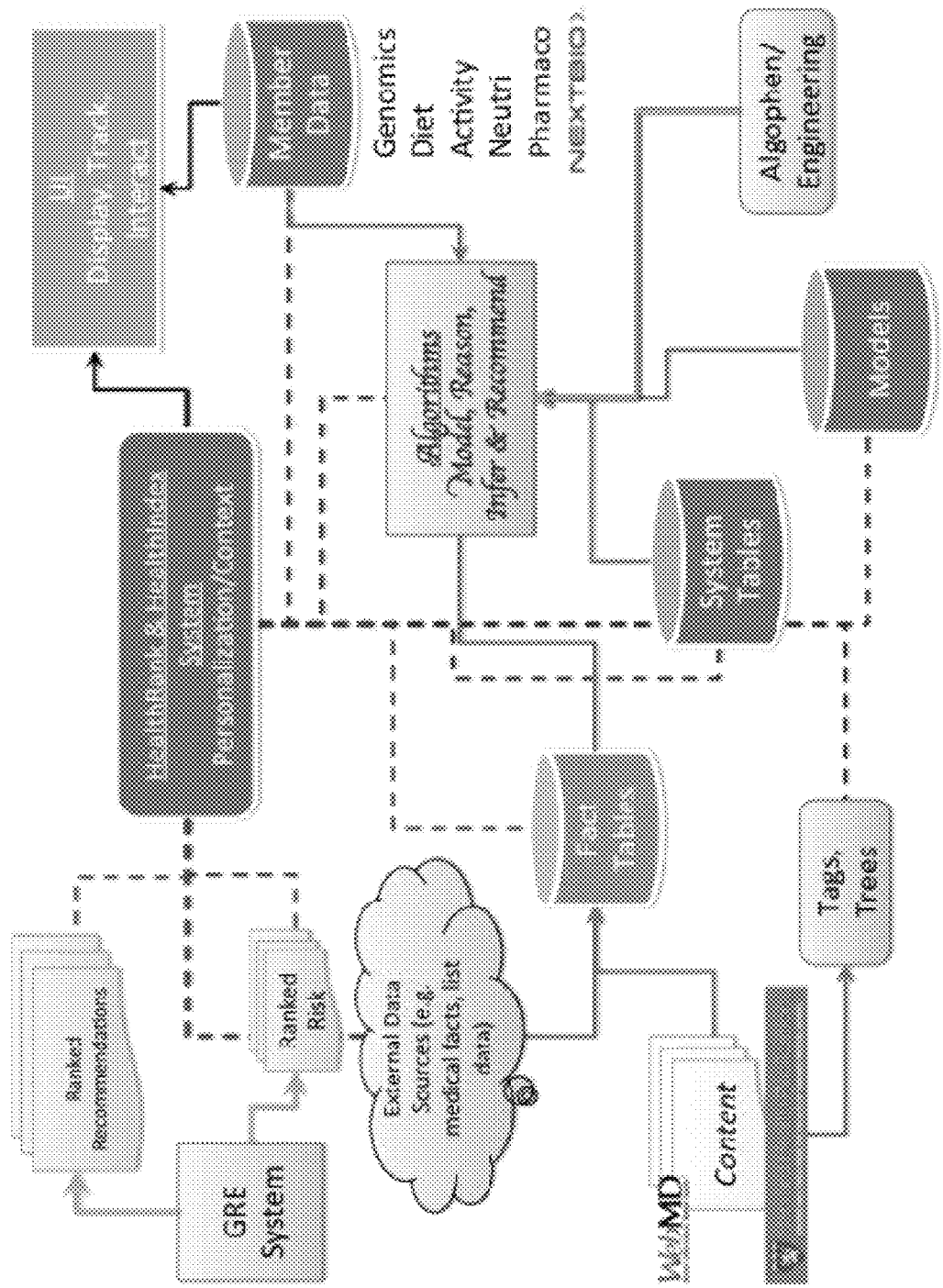
FIG. 16 is a schematic illustration showing a flowchart of the system flow for a ranking system according to certain embodiments.

FIG. 16 is a schematic illustration showing a flowchart of the system flow for ranking. Certain embodiments can include a scoring and ranking system for a set of health-related items such as scientific content, news items, blog posts, and forum discussions. The system can apply advanced data science from the domains of search, tagging, natural language processing (NLP), graph theory, ranking theory, federated informatics especially to genetics and content syndication. The goal of the system can be to present a list of ranked content for a user to read, follow, and use for behavior modification. The system can be viewed as a syndicated content contextualization and personalization, at the semantic level, in the heath domain. The concepts can be broadly applied to any domain that can be modeled in this fashion, for example to personalized scientific search.

The system can measure the relevance of a piece of information with respect to a set of different dimensions. The system can give a user contextual, personalized, and ranked content. The personalized content can be based on the user's genetics and GRE recommendations.

The system can assign a rank score, which can be a combination of numeric, alphanumeric and enumeration, to a piece of information based on a series of semantic overlays pertaining to the health, lifestyle, medical and genetics domain as follows. The following order is just one example of a possible sequence.

First, the system can assign roles, including public, member, physician, and researcher. Next, the system can assign media types: video, audio, document and image, for example. While the media type can be indicated by the file type or extension, a few usability semantics can be derived from the media type. Then, the system can assign a size category, such as abstract, summary, detailed, or outline, to the information slice.

The system can then employ ranking that is not just a sort based on a maximum number of links. Furthermore, the system can provide flexible content syndication including linking, summary and embedding. Moreover, the system can provide multi-overlay based tagging and personalization, as described herein. The system can further apply collaborative filtering and clustering overlays to increase the resolution and personalization.

Various data structures, fact tables, and system tables can be used in connection with certain embodiments. For example, fact tables may include the following risk fact table elements: name, categories, normal max, normal min, absolute max, absolute min, desired value, desired direction, weight, probability, model pointer, recommendation pointers, and personalized attributes. The personalized attributes can include value, cost function type, and cost function constants-model attributes. There can be a set of standard cost functions, for example linear, table lookup, and the like. The cost might be different based on race or other factors.

Figure 17:
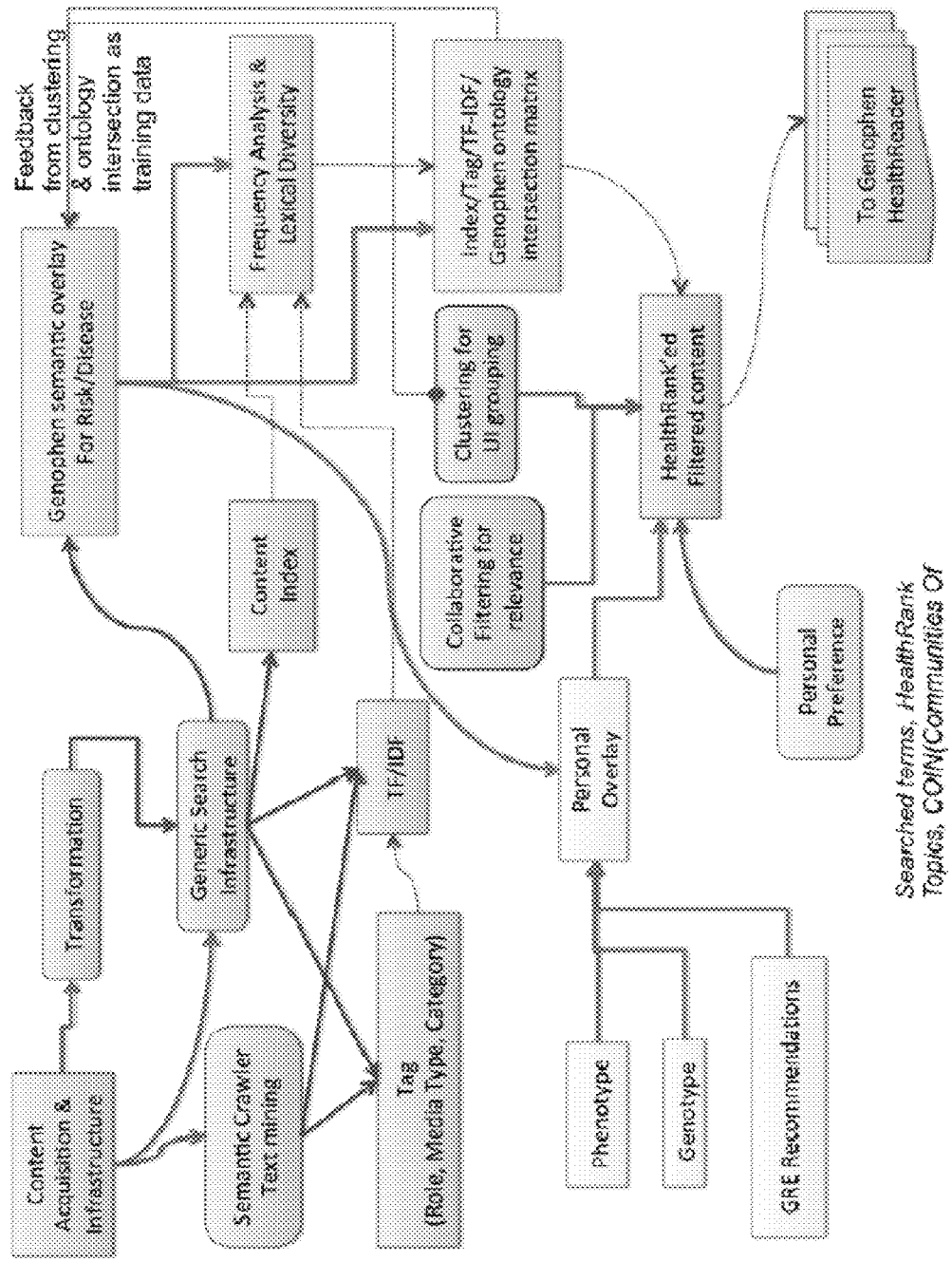
FIG. 17 is a schematic illustration showing a flowchart of the content infrastructure according to certain embodiments.

FIG. 17 is a schematic illustration showing a flowchart of a content infrastructure. The figure lists each content source and how it can be sourced, searched, tagged, and incorporated into a particular ranking system.

The system can, as mentioned above, first apply a generic search to index the content and can then apply a series of overlays to provide de-normalized trees.

The application of the generic syntax overlay with a series of semantic overlays can add to the personalization of the content, because the semantic overlays can be personalized based on a user's genetics, phenotypes, and term preferences. The ranking level can be derived from each layer. Thus, ranking can go up or down after each overlay, thereby keeping layer integrity and independence.

Certain embodiments, therefore, can effectively search for local maxima in the context of a given overlay and then derive a global maximum across the overlays as a whole. The various items of content can be displayed in the order of decreasing rank in the given context.

Among the functions of certain embodiment are content acquisition and transformation. This acquisition and transformation can include applying source level tags, for example "Hot Off the Press" and "Trivia" and applying host level categorization, such as "scientific". The acquisition and transformation can also include applying media type categorization, such as "video" or "text".

The functions can also include indexing using a generic search infrastructure. The first level indexing can be performed on the syntax using generic search infrastructure. This can yield the system a litany of terms that are stemmed, de-pluralized, and so on, from a specific document or web page or paper.

The functions can also include a semantic crawler with tagging and term frequency/inverse document frequency (TF/IDF). Then the document can be weighed against the scientific corpus to place the document in a scale. Furthermore, a semantic overlay can be applied to get a generic rank of each document. This can provide a location for the document in the concept tree. The document might be in multiple concepts and a weight can be applied to calculate the relative positioning of the document. Multiple concepts are allowed in calculations of certain embodiments. The system can also derive the content scale in terms of scientific, disruptive, and system-specific confidence.

Frequency analysis and lexical diversity can be a combined processing unifying the raw semantics from a generic search infrastructure and a risk semantic overlay. While in the previous step the system can derive the position of the document in the overlay, in this step the system can derive how close the item/document is to the concepts. This step can separate a very general document from a specific document and can rank accordingly. It can also rank the documents on the scientific rank: lexical diversity/focus of the layman vocabulary will rank the document/item lower in scientific content and vice versa.

Next, from an intersection matrix the system can derive inverse semantic overly augmentation. This derivation can be the feed-forward loop of content mining. Once the content scale is derived, the system can then mine the document index for more similar terms to update the semantic tree overlay. For example, if a document comes high on one term, ten top words can be added to that term from the document into the overlay tree dynamically. Also, if a document is highly ranked in scientific, ten top terms can be added to the scientific vocabulary of the semantic overlay tree. In these cases, the selection of ten terms is one example; other examples include five and twenty terms.

The system can also apply a personal overlay based on a user's profile. For example, when a new user's genetic information is added to the user profile, the system can dynamically create a topic tree based on specific genetic risk factors present and then search. If a user's blood pressure (BP) is high, the system can recommend content that addresses that. This level of understanding can be derived from the risk fact table and the score of the person, thus personalizing the content.

Next, the system can apply a personalized GRE overlay. At this stage, the system can apply the personalized recommendation for this user (who can be referred to as a member), assigning a rank based on the recommendations.

Furthermore, the system can apply collaborative filtering. At this stage, a rank can be derived based on how other people have interacted with the document. For example, if the document is tagged "Reference" by many, this might be a reference-able document. If all doctors read an article, it is likely more to be scientific and suited for a physician role and vice versa. The filtering can also consider metrics like top this week, top this month, and top this year for each role, as well as across all roles, and can assign appropriate rank for the document.

Because of personalization, the system can consider the genetics and personalization of the collaborative filter readers. For example, if an article on type 2 diabetes (T2D) is popular among other T2D risk members, this may be a good indication of relevance if a current member has similar risk factors. Not only the subject but also the raw affinity for a document for a genetic profile and risk can be determined.

The system can then add back personal preference from search terms customization. Thus, the system can go back to the semantic overlay trees and add back the rank based on what else this member wants to read about.

After that, the system can apply a tag filter. The tag filter can rely on tags like "Reference" or "Inbox" or on arbitrary user-generated tags or the like.

Next, the system can calculate the effective rank for this document and can use this rank along with the tags to determine the position of this document in the member's list display.

Finally, the system can apply clustering. Using similarity metrics, the system can cluster documents that have the same rank and tags. This can give a grouping for a user interface (UI). This can also give an indication of the effectiveness of the overlay. Hence, the clustering results can be used as feedback into the overlay tree to improve the effectiveness of the overlay tree.

Figure 18:
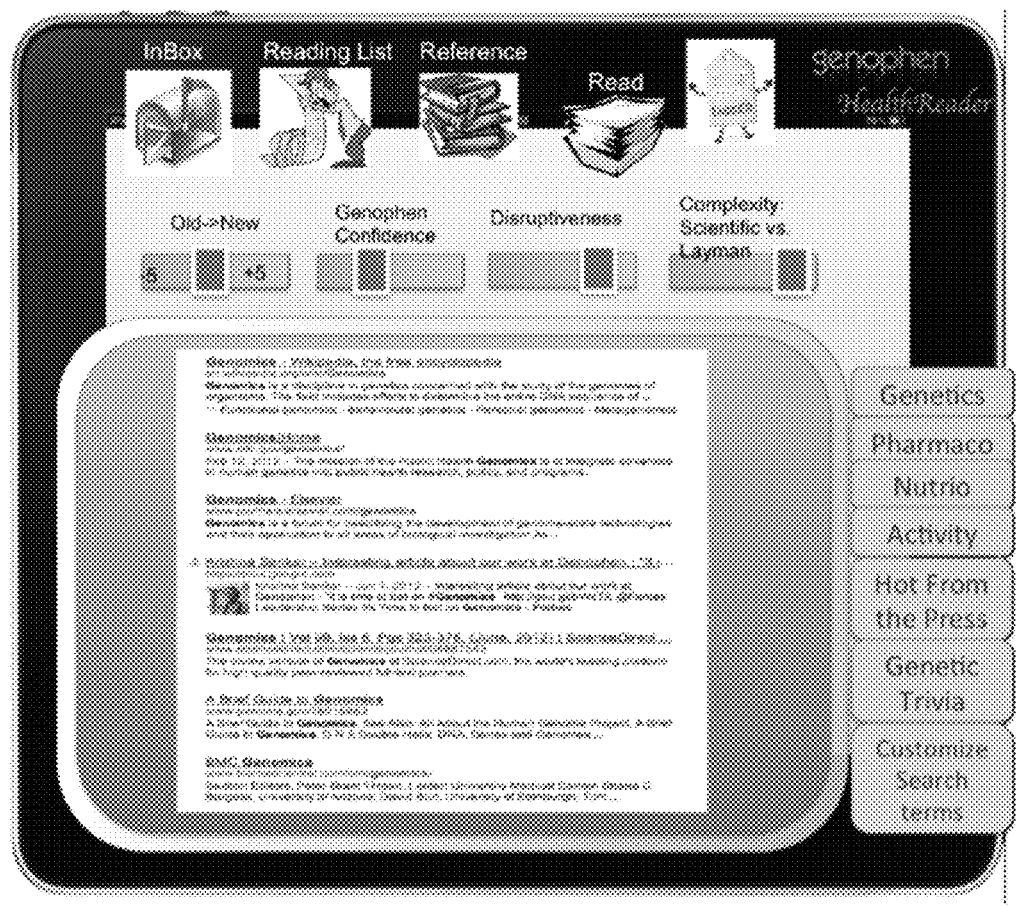
FIG. 18 is a schematic illustration showing a screenshot of a main screen of a particular reading application according to certain embodiments.

FIG. 18 is a schematic illustration showing a screenshot of the main screen of a particular reading application. Certain embodiments can include a rank reader. Internally, everything can have a tag. Readers can mark items as "Reference", "Reading List" (to be read later), or even arbitrary tags. There can also be tags such as, "Read" (items read in the past), "Inbox", and "Outbox". In addition to genetics, diet, exercise, pharmacology, and nutrition, there can also be categories like "Hot Off the Press" and "Daily Trivia".

Figure 19:
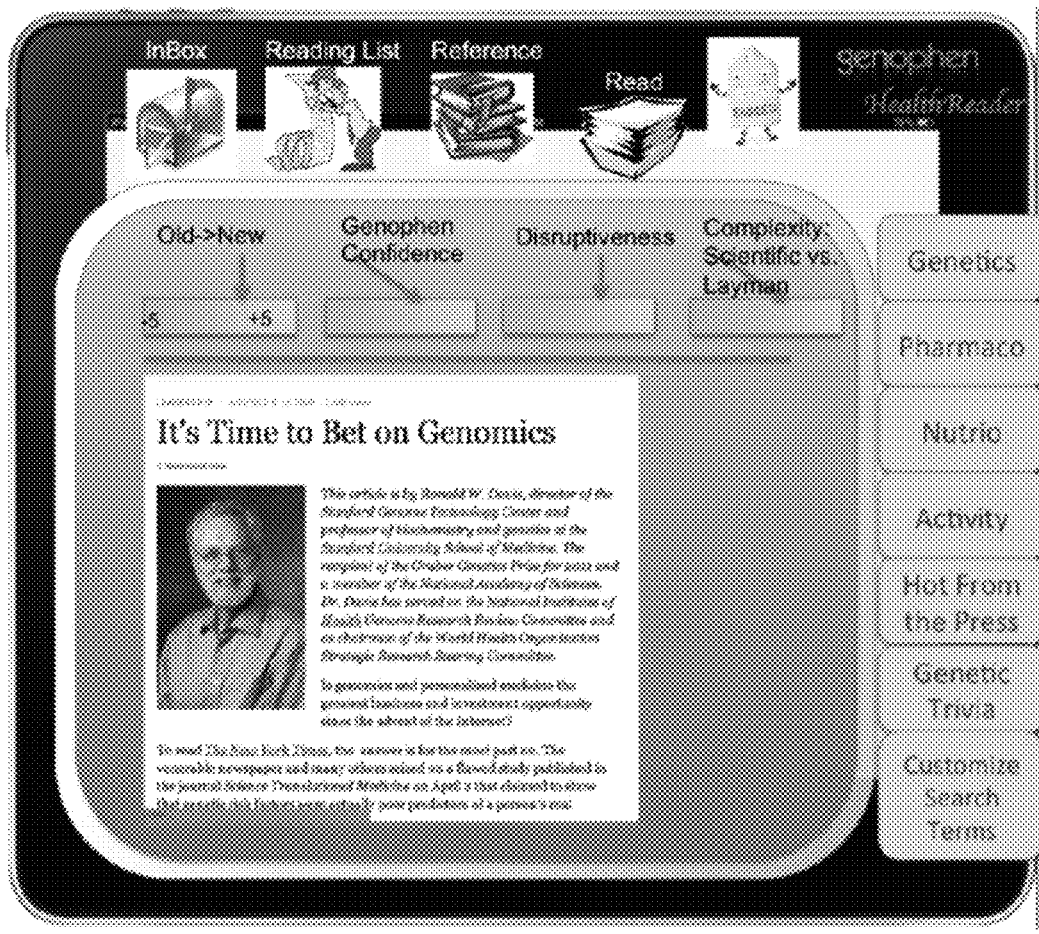
FIG. 19 is a schematic illustration showing a screenshot of a content screen of a particular reading application according to certain embodiments.

FIG. 19 is a schematic illustration showing a screenshot of the content screen of a particular reading application. There can also be scale sliders and appropriate calculated ranks for the following: age, from old to new, based on date; confidence level, indicating a system-specific confidence level of an information item; disruptiveness, an indication of how radical the ideas in an article are; and public-member-scientific scale, indicating a depth of coverage.

Figure 20:
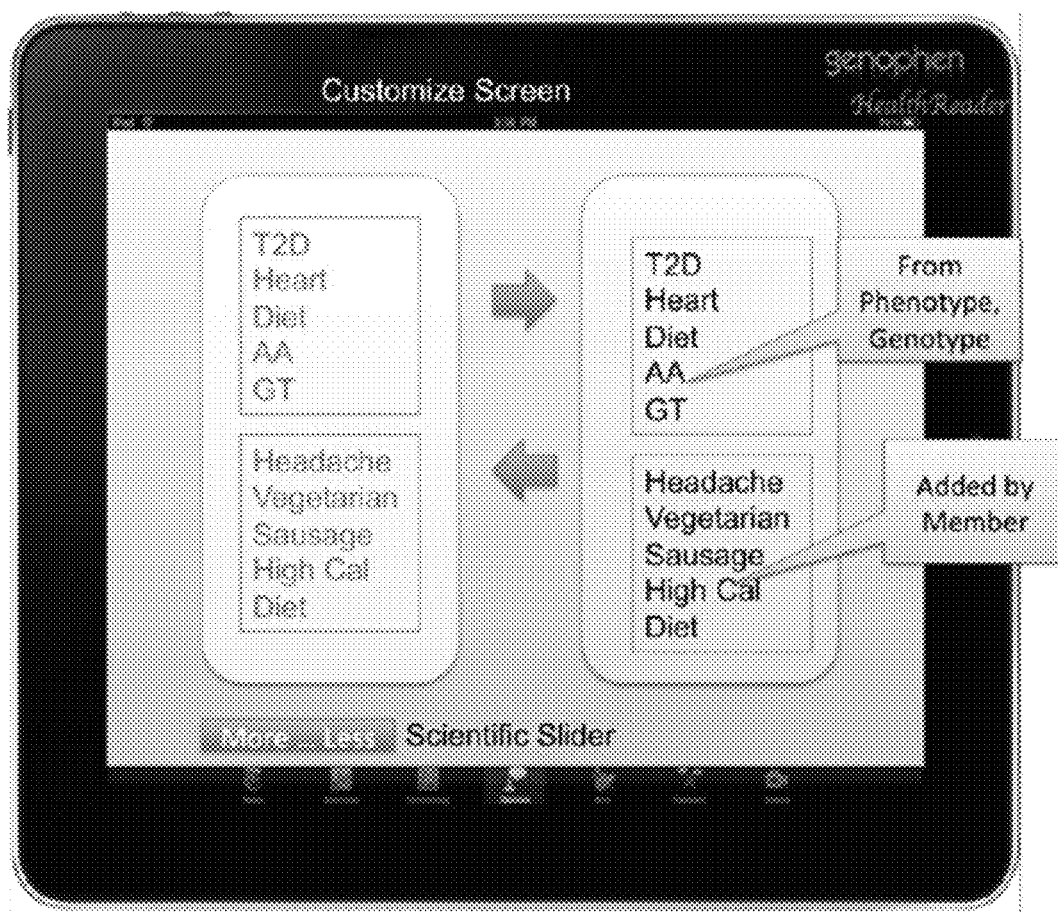
FIG. 20 is a schematic illustration showing a screenshot of a customize search terms screen of a particular reading application according to certain embodiments.

FIG. 20 is a schematic illustration showing a screenshot of the customize search terms screen of a particular reading application. There can also be tagging capabilities for Reference, Reading List (to be read later) and Arbitrary tags. Once read, the information can be moved to the read box. An inbox can have the current "To Read" items.

Figure 21:
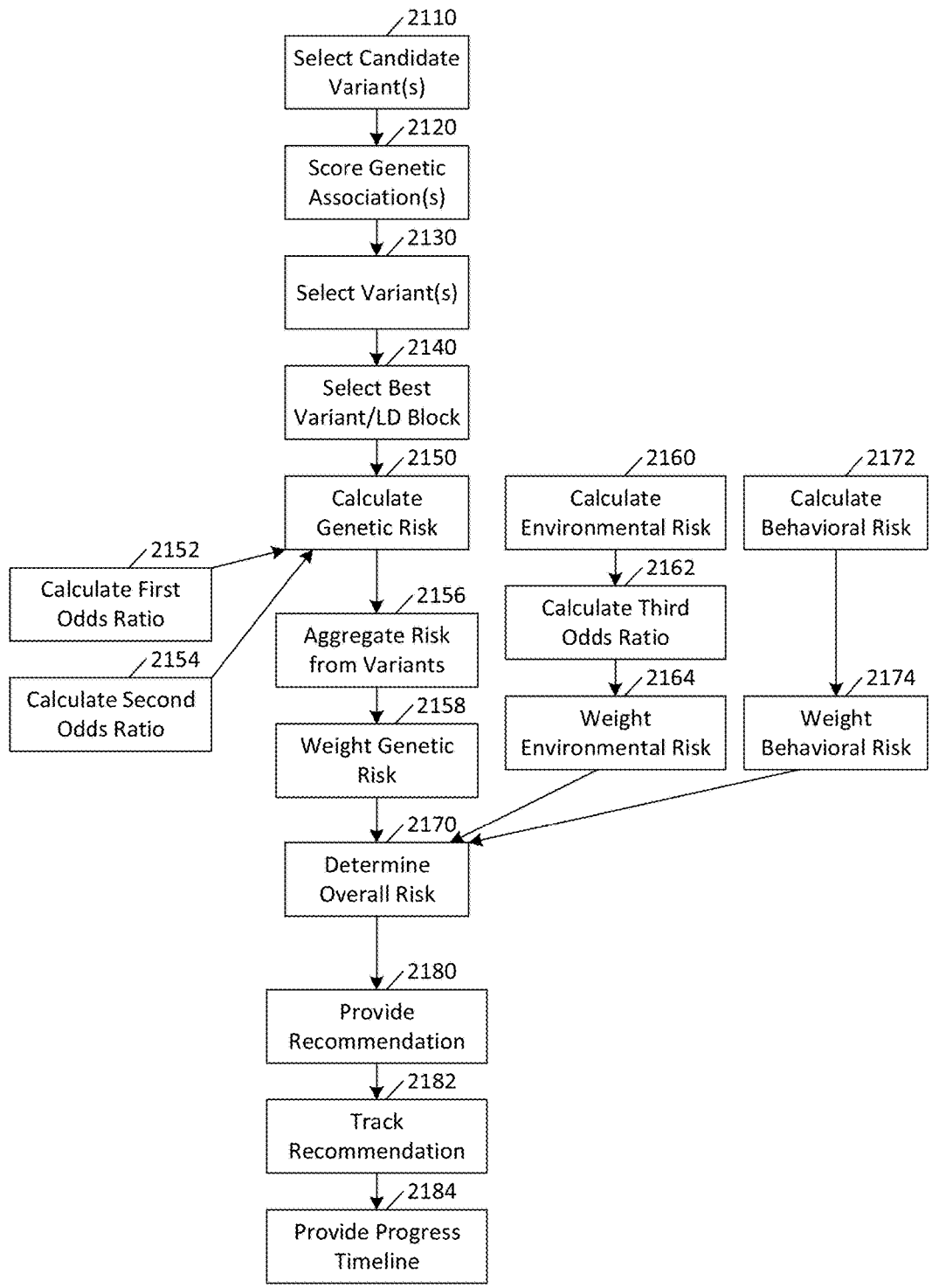
FIG. 21 illustrates a method according to certain embodiments.

FIG. 21 illustrates a method according to certain embodiments. As shown in FIG. 21, a method can include, at 2110, selecting one or more candidate genetic variants associated with a phenotype, or a combination of phenotypes, from the scientific literature. The method can also include, at 2120, scoring at least one genetic association between the one or more candidate genetic variants and the phenotype(s). The method can further include, at 2130, selecting one or more high-scoring genetic variants. The method can additionally include, at 2140, selecting a best genetic variant within at least one linkage disequilibrium (LD) block. It is possible for more than one best genetic variant to be selected, although as mentioned above, a single genetic variant can be representative of others in the block.

The method can further include, at 2150, calculating risk associated with the best genetic variant(s) from the at least one LD block. The calculation of the risk can include, at 2152, calculating a first odds ratio of a genetic variant. The calculation of the risk can also include, at 2154, calculating a second odds ratio of a haplotype or at least one further genetic variant or both.

The method can also include, at 2156, aggregating genetic risk associated with a plurality of genetic variants prior to determining the overall risk. The method can further include, at 2158, weighting the genetic risk associated with the plurality of genetic variants.

The method can further include, at 2160, calculating a risk based on environmental factors. The calculation of the risk based on the environmental factors can include, at 2162, calculating a third odds ratio associated with the environmental factors. The method can additionally include, at 2164, weighting the risk based on the environmental factors. The weighting of the risk based on the environmental factors can include weighting aggregated environmental risk from a plurality of environmental factors.

The method can also include, at 2172, calculating a risk based on behavioral factors. The method can further include, at 2174, weighting the risk based on the behavioral factors. The weighting of the risk based on the behavioral factors can include weighting aggregated behavioral risk from a plurality of behavioral factors.

The method can further include, at 2170, determining an overall risk based on the risk associated with the best genetic variant from the at least one LD block, the risk based on the environmental factors, and the risk based on the behavioral factors.

The method can also include, at 2180, providing at least one behavior modification recommendation based on the combined risk. The method can additionally include, at 2182, tracking a patient's recommendation over time. The patient's recommendation can be the recommendation made to the patient. The method can further include, at 2184, providing a timeline of progress over time based on the tracking.

Figure 22:
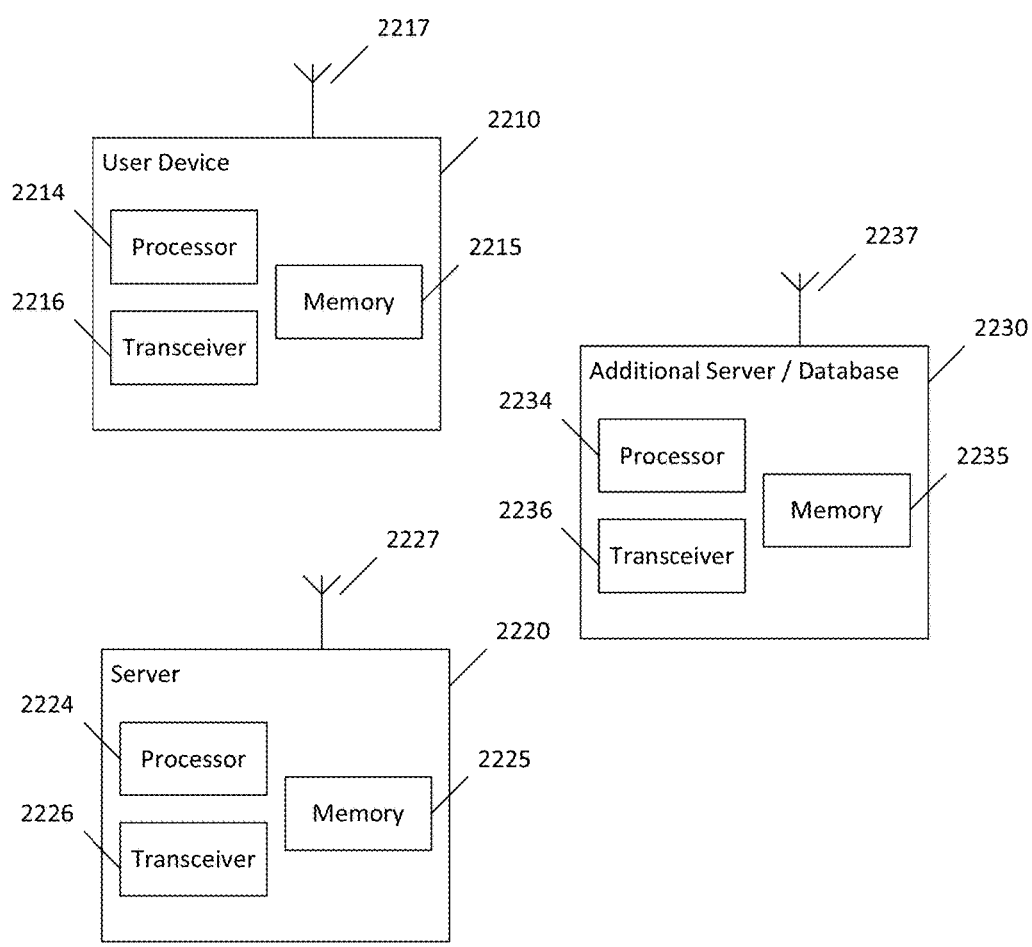
FIG. 22 illustrates a system according to certain embodiments.

FIG. 22 illustrates a system according to certain embodiments of the invention. In one embodiment, a system may include multiple devices, such as, for example, at least one user device 2210, at least one application server 2220 or other device for running the various engines described above, and at least one additional server or database 2230. In certain systems, only user device 2210 and application server 2220 may be present, and in other systems user device 2210, application server 2220, and a plurality of other servers may be present. Other configurations are also possible. The additional server or database 2230 may be, for example, a database securely storing medical records, facts, and recommendations.

The at least one user device 2210 can be a smartphone, tablet, portable computer, laptop computer, or other computing device. The user device 2210 can be provided with a graphical user interface and inputs, such as a touch-sensitive screen, keyboard, mouse, or the like. Other features are also permitted on the user device 2210. The user device 2210 can be a terminal device.

Each of these devices may include at least one processor, respectively indicated as 2214, 2224, and 2234. At least one memory can be provided in each device, as indicated at 2215, 2225, and 2235, respectively. The memory may include computer program instructions or computer code contained therein. The processors 2214, 2224, and 2234 and memories 2215, 2225, and 2235, or a subset thereof, can be configured to provide means corresponding to the various blocks of FIGS. 1, 4, 5, 10-17, and 21. Although not shown, the devices may also include additional accessories and peripherals, such as security accessories, printers, and keyboards.

As shown in FIG. 22, transceivers 2216, 2226, and 2236 can be provided, and each device may also include at least one antenna, respectively illustrated as 2217, 2227, and 2237. Other configurations of these devices, for example, may be provided. For example, user device 2210, application server 2220, and additional server or database 2230 may be configured for wired communication, rather than wireless communication, and in such a case antennas 2217, 2227, and 2237 would illustrate any form of communication hardware, without requiring a conventional antenna. For example, antennas 2217, 2227, and 2237 could correspond to network interface cards, modems, or other communication hardware.

Transceivers 2216, 2226, and 2236 can each, independently, be a transmitter, a receiver, or both a transmitter and a receiver, or a unit or device that is configured both for transmission and reception.

Processors 2214, 2224, and 2234 can be embodied by any computational or data processing device, such as a central processing unit (CPU), application specific integrated circuit (ASIC), or comparable device. The processors can be implemented as a single controller, or a plurality of controllers or processors. For example, the processors can be implemented using a single core chip or one or more multi-core chips, among other possible configurations.

Memories 2215, 2225, and 2235 can independently be any suitable storage device, such as a non-transitory computer-readable medium. A hard disk drive (HDD), random access memory (RAM), flash memory, or other suitable memory can be used. The memories can be combined on a single integrated circuit as the processor, or may be separate from the one or more processors. Furthermore, the computer program instructions stored in the memory, and which may be processed by the processors, can be any suitable form of computer program code, for example, a compiled or interpreted computer program written in any suitable programming language.

The memory and the computer program instructions can be configured, with the processor for the particular device, to cause a hardware apparatus such as user device 2210, application server 2220, and additional server or database 2230, to perform any of the processes described above (see, for example, FIGS. 1, 4, 5, 10-17, and 21). Therefore, in certain embodiments, a non-transitory computer-readable medium can be encoded with computer instructions that, when executed in hardware, perform a process such as one of the processes described herein. Alternatively, certain embodiments of the invention can be performed entirely in hardware.

One having ordinary skill in the art will readily understand that the invention as discussed above may be practiced with steps in a different order, and/or with hardware elements in configurations that are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

We claim:

1. A method of risk assessment for common health conditions, comprising:

selecting one or more valid lifestyle risk factor associated with a condition;
selecting available peer viewed scientific publications for each associated lifestyle risk factor;
scoring a significance of association between content of all the selected scientific publications per risk factor;
selecting one or more significant data point per risk factor;
calculating, using a processor, risk associated with a best selected risk factor data point;
calculating, using the processor, aggregated lifetime condition risk associated with a plurality of lifestyle, environmental and medical risk factors for each condition;
calculating, using the processor, aggregated achievable condition risk associated with none of the lifestyle, environmental and medical risk factors for each condition;
providing at least one behavior modification recommendation based on the aggregated lifetime condition risk and the aggregated achievable condition risk; and
tracking progress of a user taking action towards achieving goals associated with improving health based on the at least one behavior modification recommendation.

2. The method of claim 1, further comprising:
calculating aggregated risk associated with a plurality of each risk factor for all the conditions; and
providing at least one behavior modification recommendation based on the combined risk.

3. A method of risk assessment for common health conditions, comprising:
selecting one or more valid environmental risk factor associated with a condition;
selecting available peer viewed scientific publications for each associated environmental risk factor;
scoring a significance of association between content of all the selected scientific publications per risk factor;
selecting one or more significant data point per risk factor;
calculating, using a processor, risk associated with a best selected risk factor data point;
calculating, using the processor, aggregated lifetime condition risk associated with a plurality of lifestyle, environmental and medical risk factors for each condition;
calculating, using the processor, aggregated achievable condition risk associated with none of the lifestyle, environmental and medical risk factors for each condition;
providing at least one behavior modification recommendation based on the aggregated lifetime condition risk and the aggregated achievable condition risk; and
tracking progress of a user taking action towards achieving goals associated with improving health based on the at least one behavior modification recommendation.

4. The method of claim 3, further comprising:
calculating aggregated risk associated with a plurality of each risk factor for all the conditions; and
providing at least one behavior modification recommendation based on the combined risk.

5. A method of risk assessment for common health conditions, comprising:
selecting one or more valid medical risk factor associated with a condition;
selecting available peer viewed scientific publications for each associated medical risk factor;
scoring a significance of association between content of all the selected scientific publications per risk factor;
selecting one or more significant data point per risk factor;

calculating, using a processor, risk associated with a best selected risk factor data point;

calculating, using the processor, aggregated lifetime condition risk associated with a plurality of lifestyle, environmental and medical risk factors for each condition;

calculating, using the processor, aggregated achievable condition risk associated with none of the lifestyle, environmental and medical risk factors for each condition;

providing at least one behavior modification recommendation based on the aggregated lifetime condition risk and the aggregated achievable condition risk; and tracking progress of a user taking action towards achieving goals associated with improving health based on the at least one behavior modification recommendation.

6. The method of claim 5, further comprising:

calculating aggregated risk associated with a plurality of each risk factor for all the conditions; and providing at least one behavior modification recommendation based on the combined risk.

\* \* \* \* \*